United States Patent
Slone et al.

(10) Patent No.: US 7,959,091 B2
(45) Date of Patent: *Jun. 14, 2011

(54) MOBILE FOAM PRODUCING UNIT

(75) Inventors: Joe D. Slone, Greensboro, NC (US); Nicolas A. Granucci, Greensboro, NC (US); David E. Sugg, Cornelius, NC (US)

(73) Assignee: Ecolab USA Inc., St. Paul, MN (US)

( * ) Notice: Subject to any disclaimer, the term of this patent is extended or adjusted under 35 U.S.C. 154(b) by 121 days.

This patent is subject to a terminal disclaimer.

(21) Appl. No.: 12/422,329

(22) Filed: Apr. 13, 2009

(65) Prior Publication Data

US 2009/0194178 A1 Aug. 6, 2009

Related U.S. Application Data

(63) Continuation of application No. 11/744,483, filed on May 4, 2007, now Pat. No. 7,516,907.

(51) Int. Cl.
*B05B 9/03* (2006.01)
(52) U.S. Cl. ......... 239/146; 239/172; 239/135; 239/407
(58) Field of Classification Search .................. 239/146, 239/172, 128, 129, 130, 131, 132.1, 133, 239/132.5, 136, 138, 137, 135, 132.3, 139, 239/398, 407, 408, 409, 410, 411, 412, 413, 239/414, 147
See application file for complete search history.

(56) References Cited

U.S. PATENT DOCUMENTS

| | | | |
|---|---|---|---|
| 3,549,849 A | * | 12/1970 | Boehm Helmut ............ 219/748 |
| 3,704,553 A | | 12/1972 | Hehr et al. |
| 4,207,649 A | * | 6/1980 | Bates .............................. 15/319 |
| 4,366,081 A | | 12/1982 | Hull |
| 4,383,935 A | | 5/1983 | Hull |
| 4,505,431 A | | 3/1985 | Huffman |
| 4,925,109 A | | 5/1990 | Flanagan et al. |
| 4,940,082 A | * | 7/1990 | Roden ............................. 15/321 |
| 5,029,758 A | | 7/1991 | Chayer |
| 5,085,371 A | | 2/1992 | Paige |
| 5,213,263 A | | 5/1993 | Corona |
| 5,230,368 A | | 7/1993 | Berfield |
| 5,419,495 A | | 5/1995 | Berfield |
| 5,655,713 A | | 8/1997 | Gibney et al. |

(Continued)

FOREIGN PATENT DOCUMENTS

EP 0062010 A1 10/1982

(Continued)

OTHER PUBLICATIONS

"Aerolite Reservoir —Installation & Operation Manual", *Ecolab Inc.*, 21 pages (Copyright Ecolab Inc. 2003).

(Continued)

*Primary Examiner* — Len Tran
*Assistant Examiner* — Trevor E McGraw
(74) *Attorney, Agent, or Firm* — IPLM Group, P.A.

(57) ABSTRACT

A mobile foam producing unit (10) includes a first hose and hose assembly (110) and a second hose assembly (120). Water is provided to the mobile foam producing unit (10) by a supply hose (100). A foam gun (140) provides for the dispensing of a foam. A sanitizer gun (160) provides for a sanitizing solution being dispensed with water as well as, in another mode, a rinse mode wherein only water is dispensed.

19 Claims, 22 Drawing Sheets

U.S. PATENT DOCUMENTS

| | | | |
|---|---|---|---|
| D385,494 S | 10/1997 | Balz et al. | |
| D385,799 S | 11/1997 | Balz et al. | |
| D387,285 S | 12/1997 | Balz et al. | |
| 5,695,293 A | 12/1997 | Chase | |
| 5,855,217 A | 1/1999 | John | |
| 5,884,840 A | 3/1999 | Bagnara et al. | |
| 6,109,480 A | 8/2000 | Monsrud et al. | |
| 6,113,007 A | 9/2000 | Bagnara et al. | |
| 6,206,980 B1 | 3/2001 | Robinson | |
| 6,293,294 B1 | 9/2001 | Loeb et al. | |
| 6,371,332 B1 | 4/2002 | Fox | |
| 6,394,365 B1 | 5/2002 | Jeanfreau | |
| 6,455,017 B1 | 9/2002 | Kasting et al. | |
| 6,527,196 B1 | 3/2003 | Ehrick et al. | |
| 6,571,805 B2 | 6/2003 | Hoenisch et al. | |
| 6,626,332 B2 | 9/2003 | Ehrensperger et al. | |
| 6,976,279 B1 * | 12/2005 | Berke et al. | 4/620 |
| 7,516,907 B2 * | 4/2009 | Slone et al. | 239/146 |
| 2002/0148066 A1 | 10/2002 | Bullis | |
| 2003/0034057 A1 * | 2/2003 | Liao | 134/95.2 |
| 2003/0217421 A1 | 11/2003 | Besel | |
| 2004/0040102 A1 | 3/2004 | Field et al. | |
| 2004/0069817 A1 * | 4/2004 | Jacques | 222/529 |
| 2004/0195346 A1 | 10/2004 | McIntyre | |
| 2004/0256483 A1 | 12/2004 | Guest et al. | |
| 2005/0205688 A1 * | 9/2005 | Bennett et al. | 239/146 |
| 2006/0102745 A1 * | 5/2006 | Dexter | 239/146 |
| 2007/0095938 A1 * | 5/2007 | Rioux | 239/302 |
| 2007/0187528 A1 * | 8/2007 | Roth et al. | 239/146 |
| 2008/0001007 A1 | 1/2008 | Gilpatrick et al. | |

FOREIGN PATENT DOCUMENTS

| | | |
|---|---|---|
| EP | 0 466 663 A | 1/1992 |
| EP | 1248682 A1 | 10/2002 |
| GB | 2318069 A | 4/1998 |
| WO | WO/9513885 A1 | 5/1995 |
| WO | WO/9633817 A1 | 10/1996 |
| WO | WO/9713591 A1 | 4/1997 |
| WO | WO/025047 A1 | 1/2002 |
| WO | WO/2005028132 A1 | 3/2005 |

OTHER PUBLICATIONS

Pump-up Foamer technology—Foam-iT® Cleaning Equipment, Innovative Cleaning Equipment Incorporated, www.foamit.com, 3 pages (Art known to be prior to filing of parent U.S. Appl. No. 11/744,483).

* cited by examiner

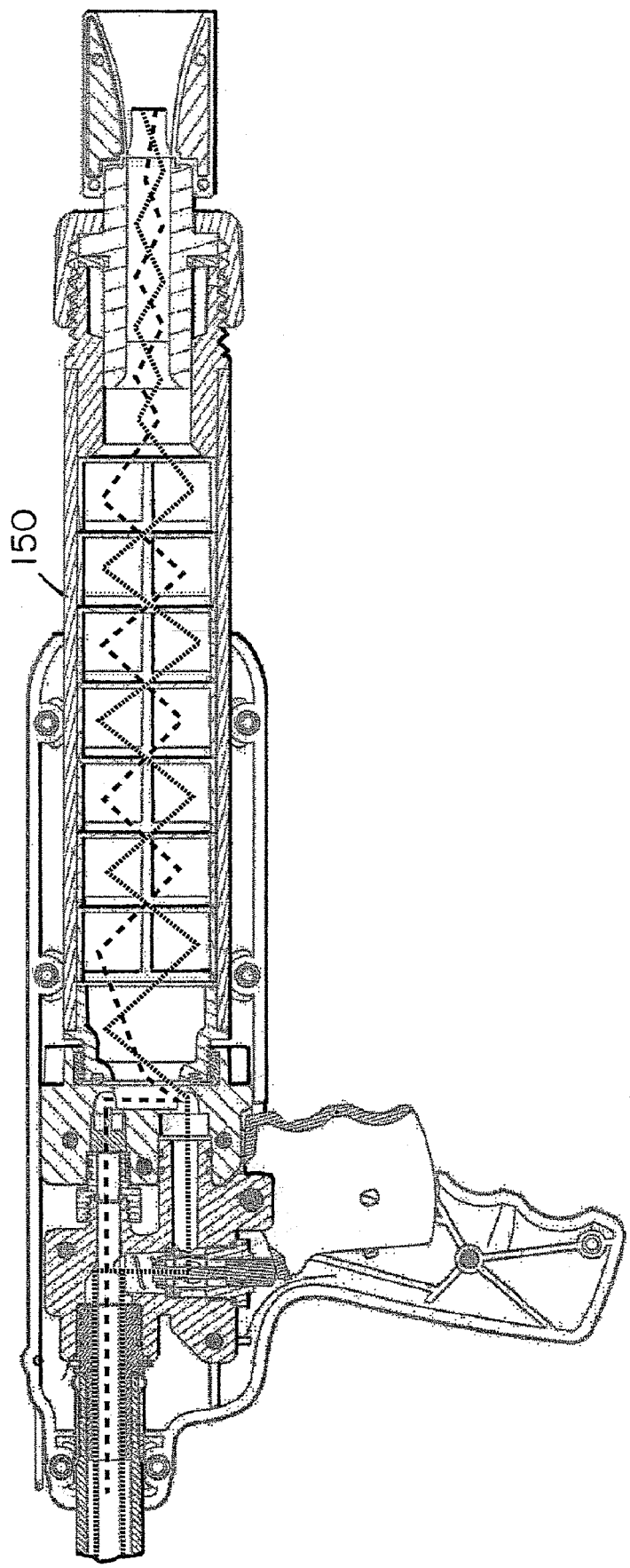

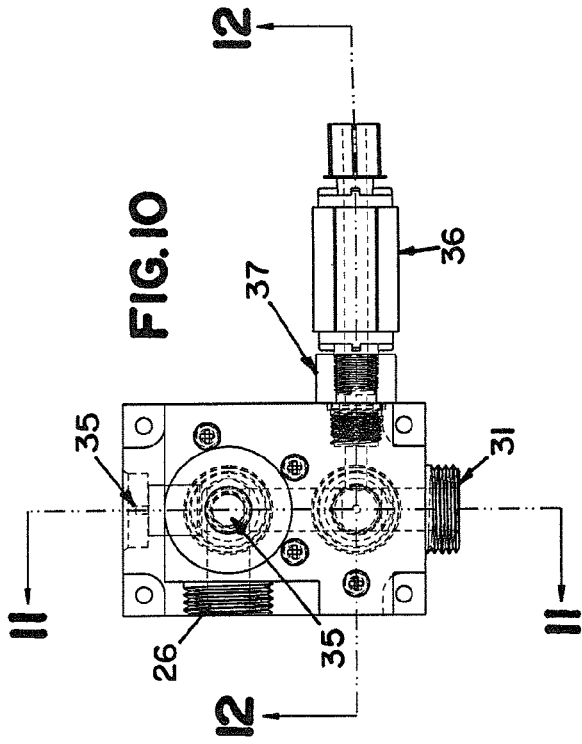
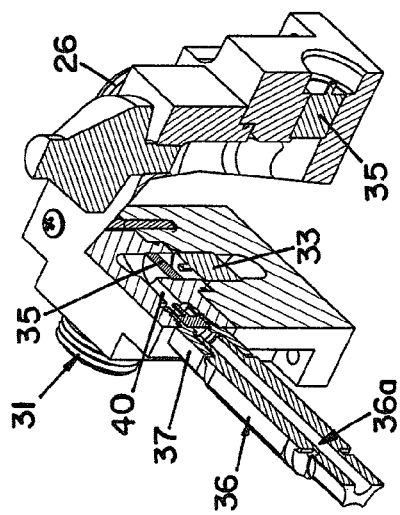
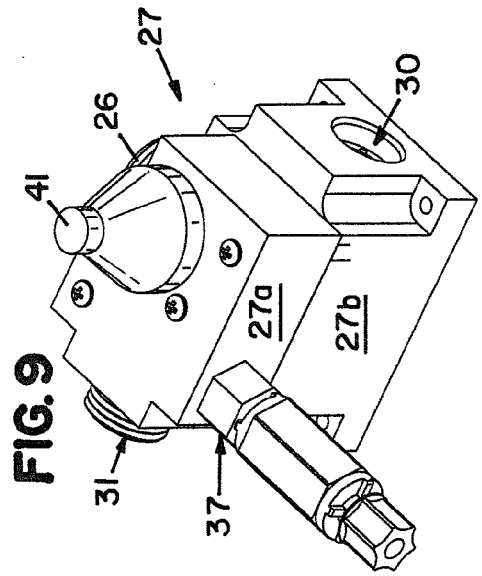
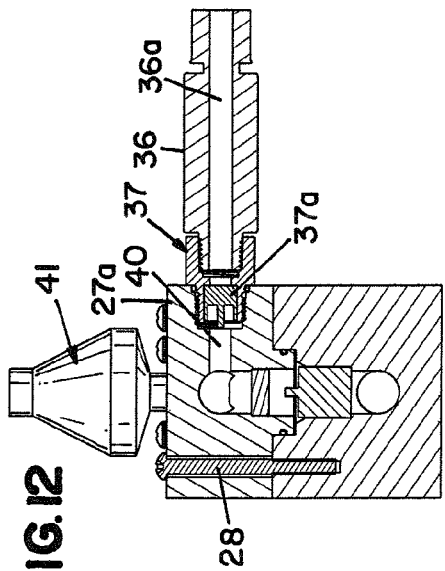
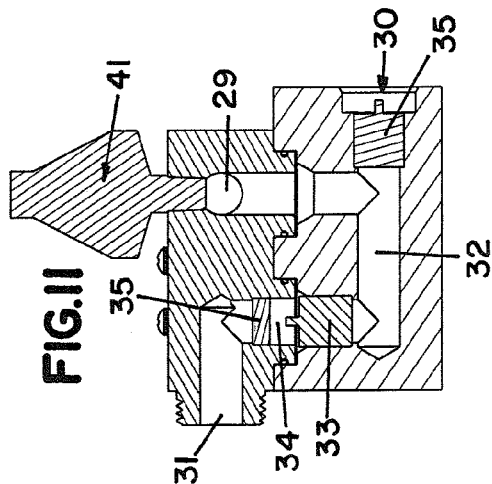

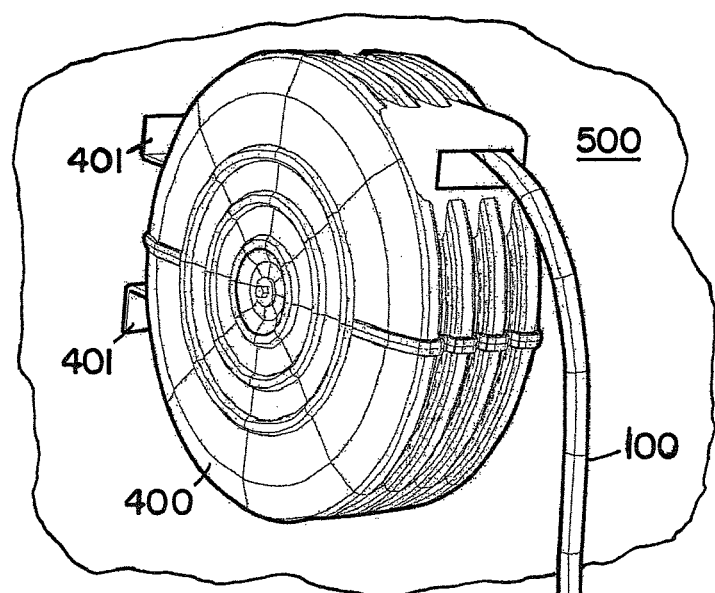
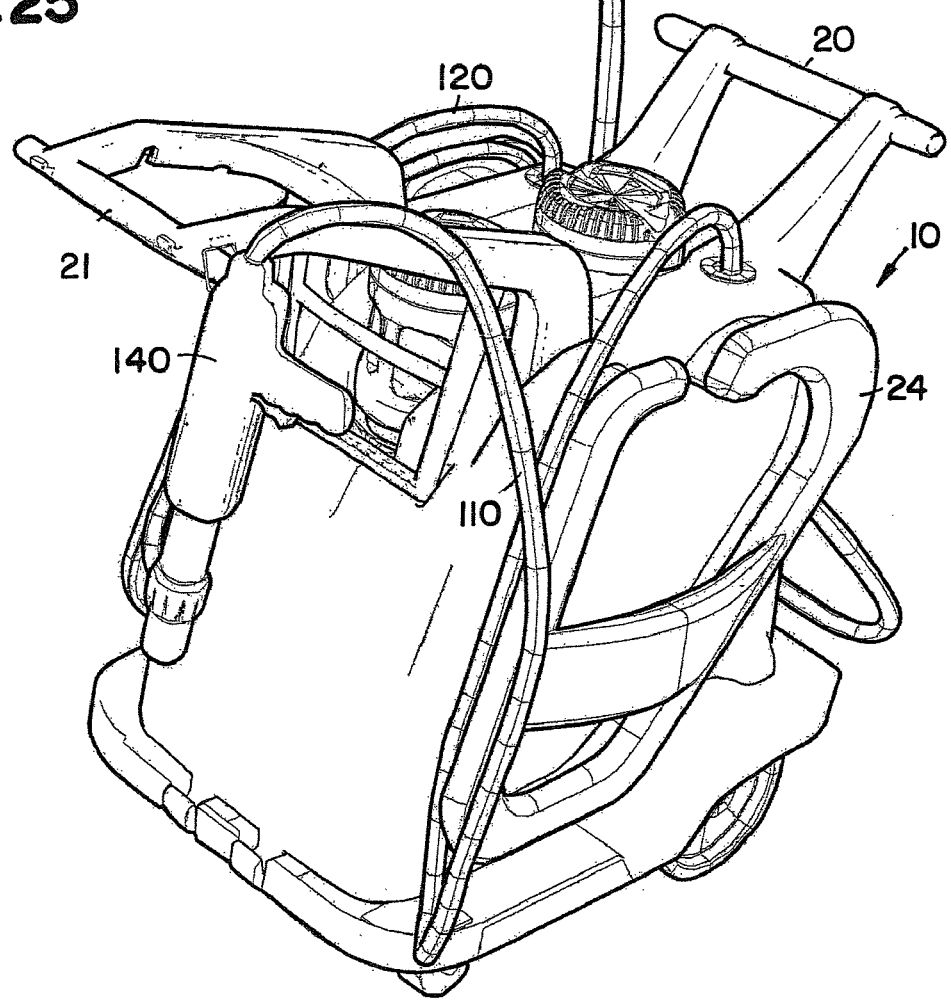
FIG. 25

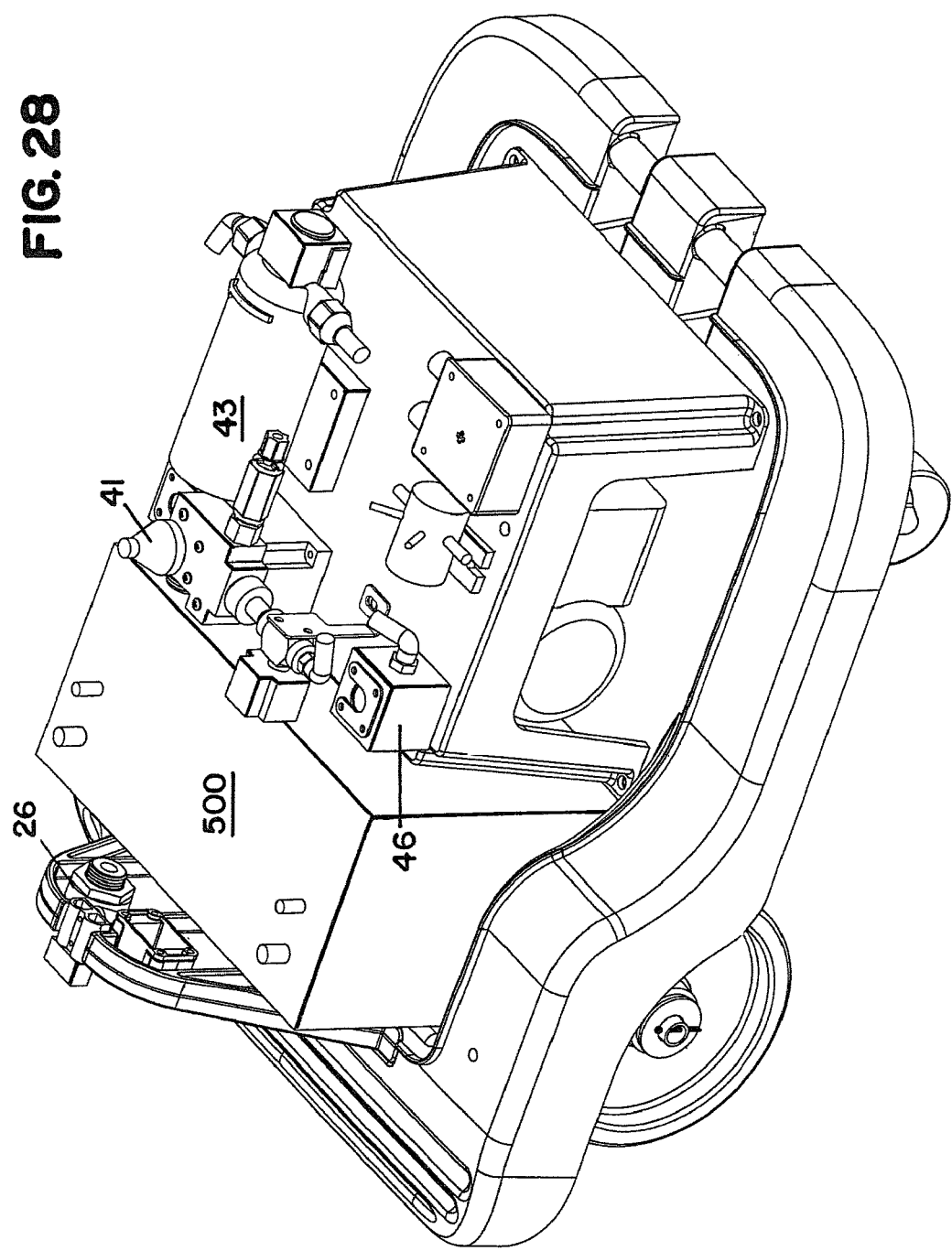

MOBILE FOAM PRODUCING UNIT

This application is a continuation of U.S. patent application Ser. No. 11/744,483, filed May 4, 2007, and entitled "Mobile Foam Producing Unit."

BACKGROUND OF THE INVENTION

1. Field of the Invention

This invention relates generally to a mobile foam producing unit for cleaning, and more particularly to a mobile foam producing unit for cleaning and sanitizing a work area.

2. Description of the Prior Art

For many cleaning situations, it is desirable to have a foam product for easier and better cleaning. One area where such cleaning is utilized is in the food retail business, such as the deli area of a large store such as Wal-Mart or the like. In addition to cleaning, it is also desired to sanitize the work area, which would also include rinsing away the chemicals used in the cleaning and sanitizing. Such an operation necessarily has involved the use of several hoses, creating problems with hose management and simply having the hoses not getting in the way of the cleaning operation.

Further, in generating a high quality foam, it is often desirous to have a high pressure source of air and/or water. However, such high pressure sources cause safety concerns. The present invention addresses the issues noted above and provides for a mobile foam producing unit that is applicable for cleaning and sanitizing a work area.

SUMMARY OF THE INVENTION

In one embodiment, the invention is a mobile foam producing unit for dispensing a first liquid and a second liquid using a municipal water supply providing water at a pressure of less than 100 psi. The unit includes a base having a plurality of wheels. A housing is operatively connected to the base, the housing having first, second, third and fourth sides. The housing has a first docking area for receiving a first liquid and a second docking area for receiving a second liquid. An air compressor supplies compressed air and is operatively connected to the base. A water pump, having a water pump inlet and a water pump outlet, is operatively connected to the base. A first hose assembly has a first outer hose and a first inner hose. A second hose assembly has a second outer hose and a second inner hose. A water inlet has a first opening adapted and configured to be connected to a municipal water supply and a second opening in fluid communication with the water pump inlet. A rechargeable battery is operatively connected to the base, the rechargeable battery being used to power the air compressor and the water pump. The water inlet, through the water pump, is in fluid communication with the first outer hose and the water inlet in fluid communication with the second outer hose. The first liquid is in fluid communication with the first outer hose, wherein a use solution is made. The air compressor is in fluid communication with the first inner hose. The second liquid is in fluid communication with the second inner hose. A first spray gun is operatively connected to a discharge end of the first hose assembly, whereby foam is dispensed by combining the use solution in the first outer hose and the compressed air in the first inner hose. A second spray gun is operatively connected to a discharge end of the second hose assembly, the second spray gun having a selector valve for allowing separate dispensing of the water in the second outer hose and the second liquid in the second inner hose. A first hose rack is operatively connected to a first side of the housing, wherein the first hose assembly is storable on the first hose rack. A second hose rack is operatively connected to a second side of the housing, wherein the second hose assembly is storable on the second hose rack.

In another embodiment, the invention is a mobile foam producing unit for dispensing a first liquid and a second liquid using a municipal water supply providing water at a pressure of less than 100 psi. The unit includes a base having a plurality of wheels. A housing is operatively connected to the base, the housing having first, second, third and fourth sides. The housing has a first docking area for receiving a first liquid and a second docking area for receiving a second liquid. An air compressor for supplies compressed air and is operatively connected to the base. A water pump, having a water pump inlet and a water pump outlet, is operatively connected to the base. A first hose assembly has a first outer hose and a first inner hose. A second hose assembly has a second outer hose and a second inner hose. A water inlet has a first opening adapted and configured to be connected to a municipal water supply and a second opening in fluid communication with the water pump inlet. A rechargeable battery is operatively connected to the base, the rechargeable battery being used to power the air compressor and the water pump. The water inlet, through the water pump, is in fluid communication with the first outer hose and the water inlet in fluid communication with the second outer hose. The first liquid is in fluid communication with the first outer hose, wherein a use solution is made. The air compressor is in fluid communication with the first inner hose. The second liquid is in fluid communication with the second inner hose. A first spray gun is operatively connected to a discharge end of the first hose assembly, whereby foam is dispensed by combining the use solution in the first outer hose and the compressed air in the first inner hose. A second spray gun is operatively connected to a discharge end of the second hose assembly, the second spray gun having a selector valve for allowing separate dispensing of the water in the second outer hose and the second liquid in the second inner hose. A first hose rack is operatively connected to a first side of the housing, wherein the first hose assembly is storable on the first hose rack. A second hose rack is operatively connected to a second side of the housing, wherein the second hose assembly is storable on the second hose rack. A first handle is operatively connected to the unit proximate the third side of the housing. A second handle is operatively connected to the unit proximate the fourth side of the housing, the third side opposite the fourth side, wherein the unit is capable of being separately pushed and pulled from both the third and fourth sides. The air compressor provides compressed air at less than 130 psi. The water pump provides water at a pressure of less than 100 psi. The first liquid is provided in a first bottle having a first outer configuration. The first docking area has a first cross-sectional area matched to receive the first bottle outer configuration. The second liquid is provided in a second bottle having a second outer configuration. The second docking area has a second cross-sectional area matched to receive the second bottle outer configuration, wherein a product lockout is created to prevent mixing of the liquids and the docking areas. A self-retracting hose reel is operatively connected to a support surface. A supply hose is carried by the self-retracting hose reel, the supply hose having a first end adapted and configured to be connected to the municipal water supply and a second end in fluid communication with the water inlet, wherein the mobile foam producing unit has improved hose management of the first hose assembly, second hose assembly and the supply hose.

In another embodiment, the invention is a portable system to clean and disinfect a work area using a municipal water supply providing water at a pressure of less than 100 psi, using a cleaning concentrate and a liquid sanitizer. The system comprises a base having a plurality of wheels. A housing is operatively connected to the base, the housing having a first docking area for receiving a cleaning concentrate and a second docking area for receiving a liquid sanitizer. An air compressor supplies compressed air and is operatively connected to the base, the air compressor providing compressed air at less than 130 psi. A first hose assembly has a first conduit and a second conduit, the second conduit carried by the first conduit. A second hose assembly has a third conduit and a fourth conduit, the fourth conduit carried by the third conduit. A water pump has a water pump inlet and a water pump outlet, and is operatively connected to the base. A water inlet has a first opening adapted and configured to be connected to receive water from a municipal water supply and a second opening in fluid communication with the water pump inlet. The water from the water pump outlet is at a pressure less than 100 psi. A foam spray gun is in fluid communication with the water pump outlet and the cleaning concentrate, wherein a quality foam is produced. A sanitizer gun is in fluid communication with the water inlet and the liquid sanitizer, the sanitizer gun having a selector valve for allowing the dispensing of both the water from the third conduit and the dispensing of a combination water from the third conduit and liquid sanitizer from the fourth conduit.

In another embodiment, the invention is a portable system to clean and disinfect a work area using a municipal water supply providing water at a pressure of less than 100 psi, using a cleaning concentrate and a liquid sanitizer. The system includes a base having a plurality of wheels. A housing is operatively connected to the base, the housing having a first docking area for receiving a cleaning concentrate and a second docking area for receiving a liquid sanitizer. An air compressor supplies compressed air operatively connected to the base, the air compressor providing compressed air at less than 130 psi. A first hose assembly has a first conduit and a second conduit, the second conduit carried by the first conduit. A second hose assembly has a third conduit and a fourth conduit, the fourth conduit carried by the third conduit. A water pump has a water pump inlet and a water pump outlet, and is operatively connected to the base. A water inlet has a first opening adapted and configured to receive water from a municipal water supply and a second opening in fluid communication with the water pump inlet. The water from the water pump outlet is at a pressure less than 100 psi. A foam spray gun is in fluid communication with the water pump outlet and the cleaning concentrate, wherein a quality foam is produced. A sanitizer gun is in fluid communication with the water inlet and the liquid sanitizer, the sanitizer gun having a selector valve for allowing the dispensing of both the water from the third conduit and the dispensing of a combination water from the third conduit and liquid sanitizer from the fourth conduit. The foam has a rating on a modification of foam quality test of 25 seconds or more. The foam has a unit foam ratio of 6.0 or greater.

BRIEF DESCRIPTION OF THE DRAWINGS

FIG. 8 is a cross-sectional view, similar to FIG. 7, showing a flow diagram thereof;

FIG. 9 is a perspective view of the manifold shown in FIG. 3;

FIG. 10 is a top plan view of the manifold shown in FIG. 9;

FIG. 11 is a cross-sectional view taken generally along the lines 11-11 in FIG. 10;

FIG. 12 is a cross-sectional view taken generally along the lines 12-12 in FIG. 10;

FIG. 13 is a perspective view of the manifold shown in FIG. 9, with portions broken away;

FIG. 25 is a perspective view of the mobile foam producing unit shown in FIG. 1, attached to a retractable reel mounted on a wall;

FIG. 28 is a perspective view of the mobile foam producing unit shown in FIG. 1, with the housing removed.

DETAILED DESCRIPTION OF A PREFERRED EMBODIMENT

Figure 1:
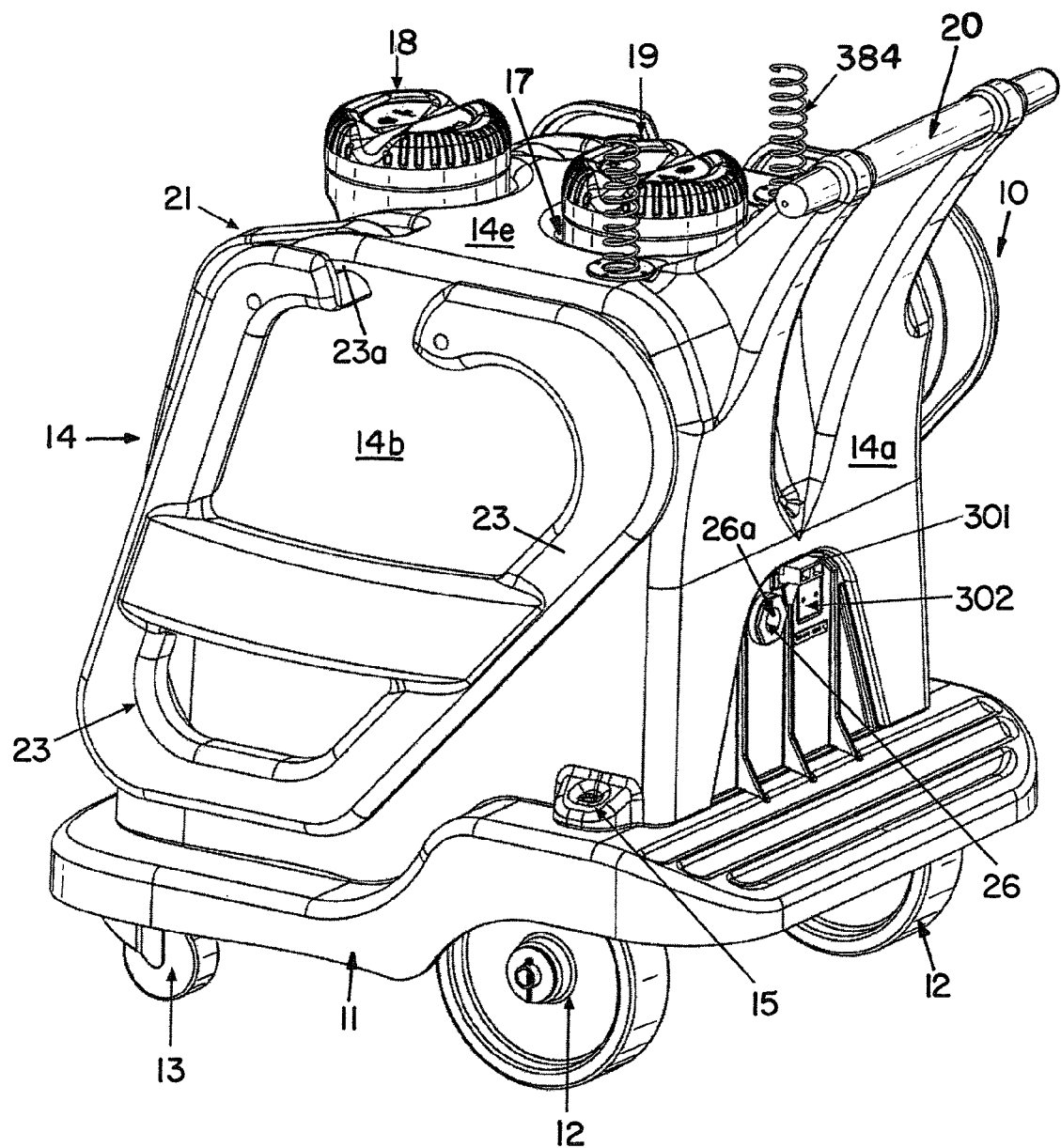
FIG. 1 is a perspective view, viewed generally from above, of a mobile foam producing unit according to the principles of the present invention.

Referring to the drawings, wherein like numerals represent like parts throughout the several views, there is generally disclosed at 10 a mobile foam producing unit. The mobile foam producing unit 10 includes a base 11 that includes two rear wheels 12 and a front swivel caster 13. The wheels 12 and 13 are operatively connected to the base by suitable means, well known in the art, and provide for the mobile foam producing unit 10 to be rolled about on the wheels 12 and 13.

A housing 14 is operatively carried by and may also be connected to the base 11 by suitable means such as bolts 15. The housing 14 may take any suitable shape and may have four sides 14a-14d all operatively connected to a top 14e to form the housing 14. As will be described more fully hereafter, the top 14e has a degreaser compartment 16 and a sanitizer compartment 17. While the compartments 16 and 17 are designated as a degreaser and sanitizer, it is understood that any suitable chemicals may be utilized. A degreaser container 18, containing a liquid degreaser is positioned in the degreaser compartment 16 and a sanitizer container 19 containing a liquid sanitizer is positioned in the sanitizer compartment 17.

Figure 3:
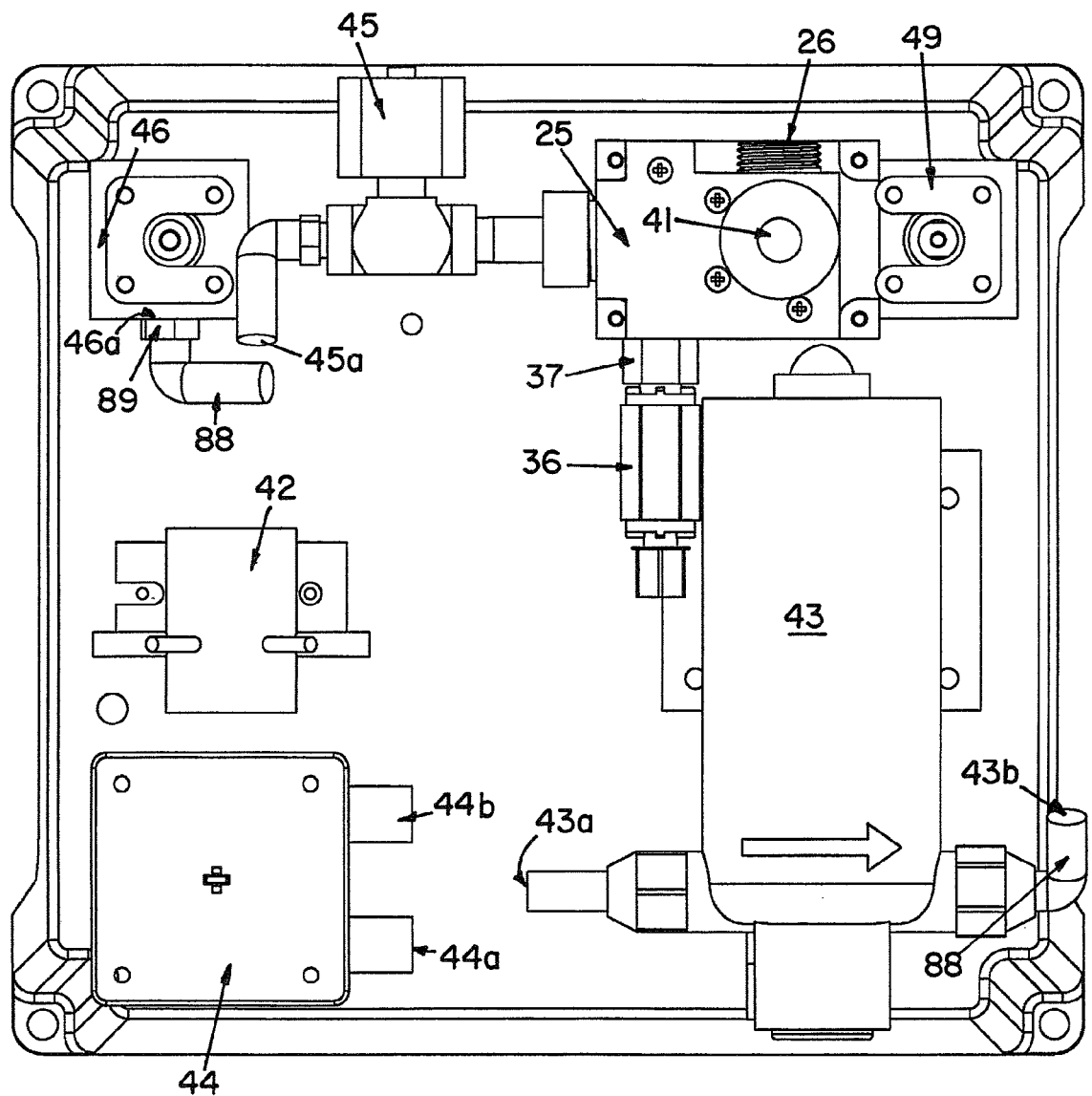
FIG. 3 is a top plan view of a portion of the mobile foam producing unit shown in FIG. 1, with the housing removed, and also shown without connecting hoses or conduits.

The lockout arrangement of the degreaser container 18 and sanitizer container 19 will be described more fully hereafter. A fixed rear handle 20 extends upward and away from the side 14a. The handle 20 may be any suitable handle and may be operatively connected to the housing 14 or base 11 by means well known in the art. Similarly, a front adjustable pull along handle 21 is operatively connected to the housing 14 by means well known in the art. The handle 21 pivots around pivot point 21a. A pivotable stand 22 pivots about point 22a in the handle 21. The adjustable handle 21 is then able to be raised and lowered. FIG. 3 shows the handle 21 raised. To lower the handle 21, the handle 21 is raised slightly and the stand 22 is pivoted so that the stand 22 pivots upward. This then allows the handle 21 to pivot about 21a and move down towards the side 14c. FIG. 1 shows the handle 21 in a down position.

A first hose rack or hose wrap 23 is operatively connected to the housing 14 and a second hose wrap or hose rack 24 is operatively connected to the housing 14 on a side opposite the first hose wrap 23. The hose wraps 23 and 24 may take any suitable shape but typically are generally rectangular in shape and form a U-shaped channel 23a and 24a in conjunction with the housing 14. The hose may then be wrapped around the hose wraps 23, 24. The top 14a(e) also has an opening 14f that may be utilized as a nozzle holder for the foam gun, as will be described more fully hereafter.

Figure 4:
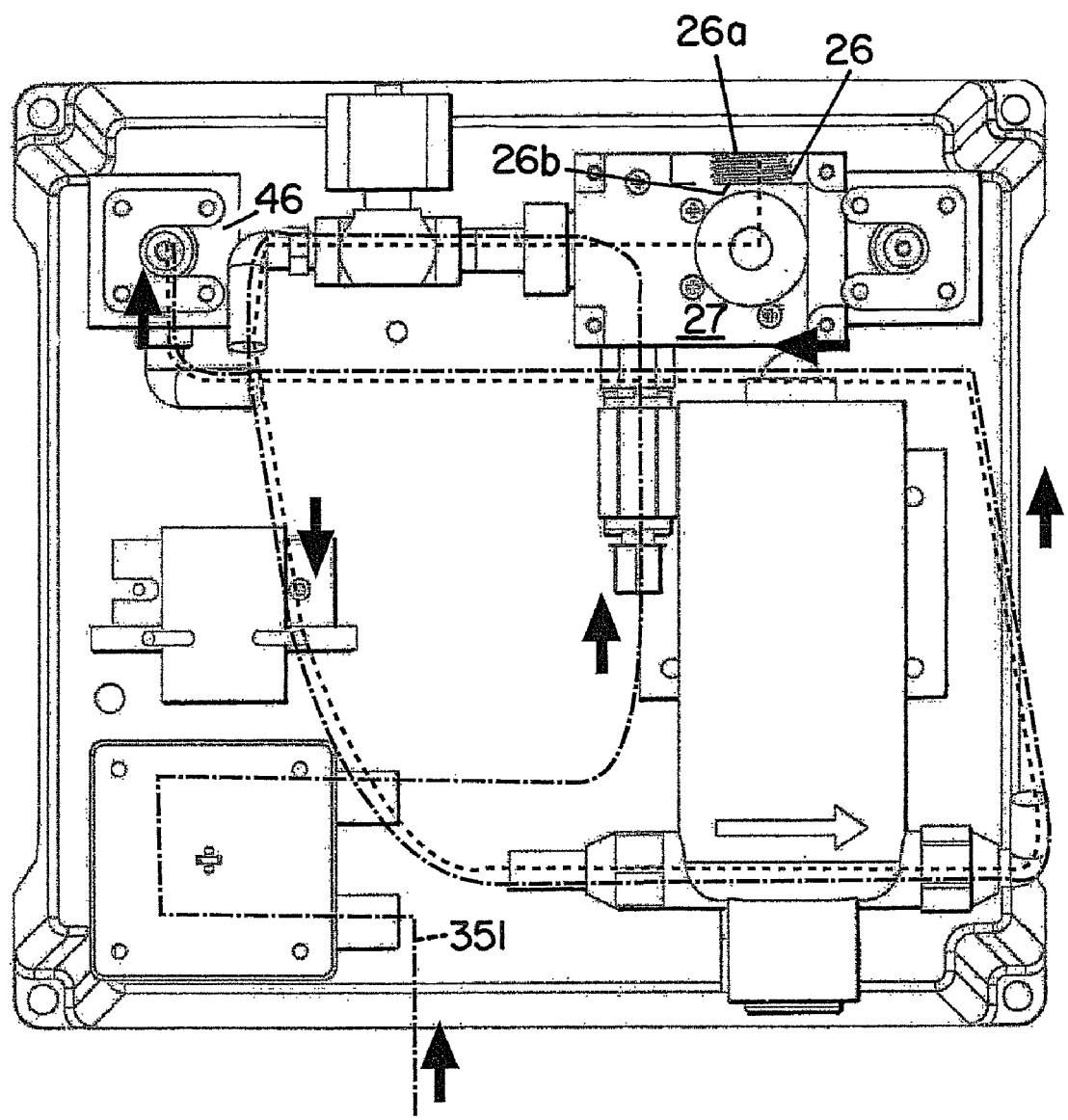
FIG. 4 is a top plan view, similar to FIG. 3, showing a flow diagram for the degreaser and water thereof.
Figure 17:
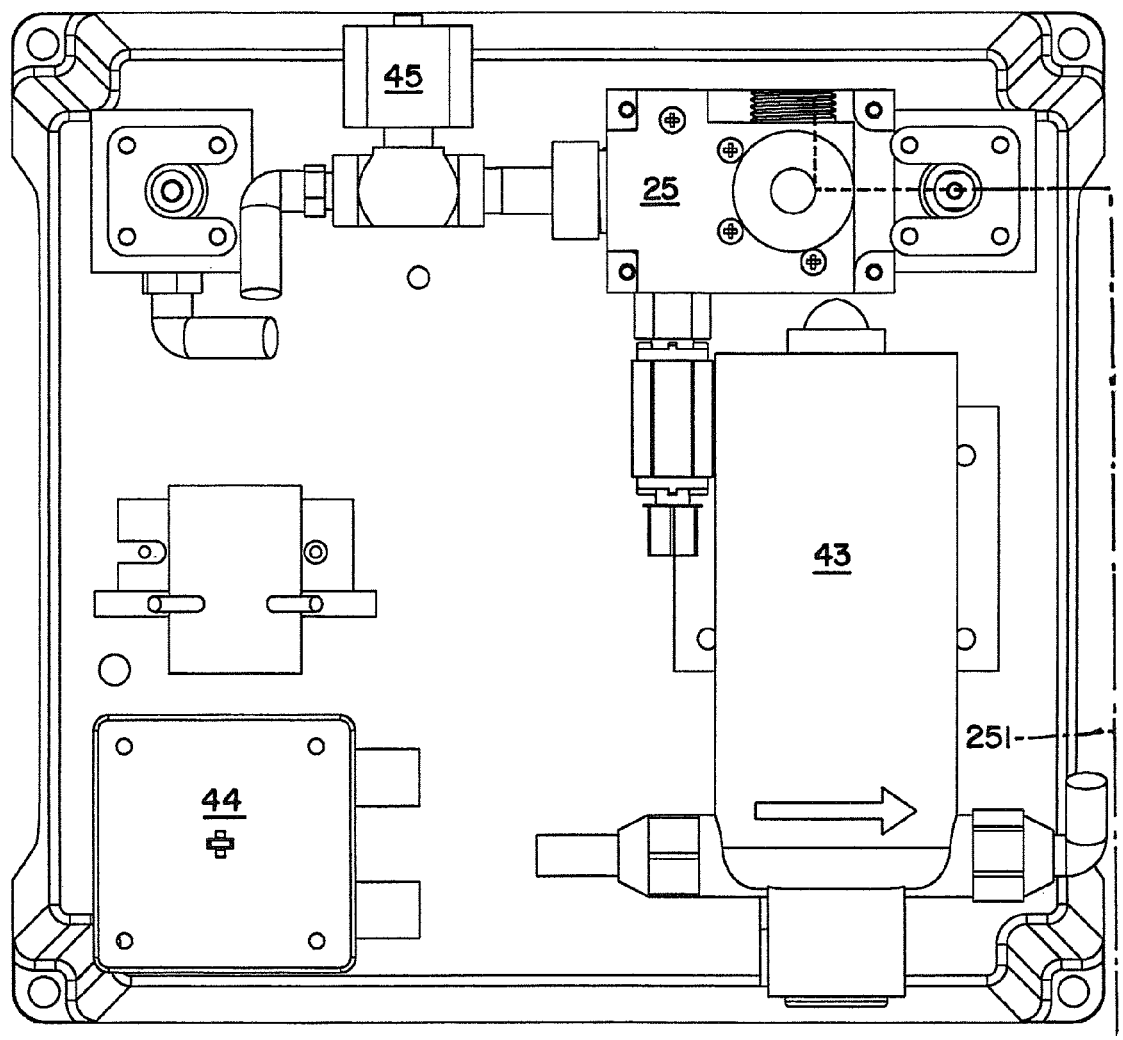
FIG. 17 is a top plan view, similar to FIG. 4, showing a flow diagram thereof for the sanitizer and water.

Referring now especially to FIGS. 3, 4 and 17, the mobile foam producing unit 10 is shown without the housing 14 to show the components more clearly. Further, the hoses or conduits that would connect the various components have been deleted for clarity. However, in FIGS. 4 and 17, flow diagrams are shown, it being obvious to one skilled in the art where appropriate hoses or conduits would be needed to place in fluid communication the various inlets and outlets as will be described in detail hereinafter. A manifold 25 has a water inlet 26. The water inlet has a first opening 26a that is in fluid communication with a supply hose 100. A second opening 26b is in fluid communication with the first opening 26a and also is in fluid communication with a manifold 27. The manifold 27 includes a top portion 27a operatively connected to a bottom portion 27b by a suitable means such as screws 28. Referring now to FIGS. 9-13, the second opening 26b is in fluid communication with a bore 29. As seen in FIG. 11, the bore 29 is in fluid communication with an outlet 30 that provides for water for a sanitizer. Water that enters the bore 29 is also in fluid communication with a degreaser use solution outlet 31. The water will go from bore 29 through bore 32. A check valve 33 is positioned in bore 34. A flow control 35 is positioned in bore 34. A flow control 35 is also positioned in the bore 32 and is utilized to control flow through the outlet 30. The flow control 35 is a suitable flow control mechanism that will control flow at a rate of 1 to 2 gallons per minute and preferably from 1.5 to 1.7 gallons per minute. An inline filter 36 by a check valve and body 37 to the top portion 27a of the manifold 27. The check valve and body 37 includes a check valve 37a. The inline filter 36 includes an inlet bore 36a through which a degreaser concentrate line is operatively connected. The bore 36a is in fluid communication with a bore 40. The degreaser concentrate that is in bore 40 will mix with the water coming up bore 34 and form a use solution that will exit the outlet 31. A water pressure sensor 41 is positioned in an opening in the top portion 27a of the manifold 27.

The water pressure sensor 41 is activated by water coming in through the water inlet 26 through bore 29. The water pressure sensor 41 is set at a minimal pressure, such as 8-10 psi. The water pressure 41 is in turn connected to a relay 42. If there is not pressure through the water inlet 26, the relay 21 does not allow for the operation of the water pump 43, peristaltic pump 44 and water cutoff solenoid valve 45. The exit 45a of the water cutoff solenoid valve 45 is connected by a suitable conduit or hose to an inlet 43a of water pump 43. The water pump 43 provides for a discharge of the degreaser use solution to the outlet 43b at a desired pressure, such as in the 40-60 psi range. The water pump 43 allows for the degreaser use solution to exit the water pump 43 at a given or desired pressure, independent of the water pressure that is entering the inlet 26. The water pressure entering the inlet 26 is dependent upon the municipal water pressure that is used. It is understood that besides a municipal water source, a well or other source may also be utilized. However, a municipal water source is used to refer to a larger water source, not included in the mobile foam producing unit. The water pressure from the municipal water source may vary. Accordingly, as will be described hereinafter, a variable water pressure would affect the quality of foam ultimately produced. By utilizing the water pump to provide a given or known pressure, the foam quality is able to be maintained from the mobile foam producing unit 10 independent of the water pressure of the municipality.

The degreaser reservoir 200 is in fluid communication with the peristaltic pump 44 by suitable means such as a conduit. The conduit is connected at one end to the outlet of the reservoir 200 and at the other end at the inlet 44a of the peristaltic pump 44. The outlet 44b of the peristaltic pump 44 is in fluid communication with the bore 36a of the inline filter 36. The degreaser concentrate is thereby supplied to the inline filter 36 and then into the manifold 27 and mixed appropriately with the water, as previously described, to form the degreaser use solution.

Figure 15:
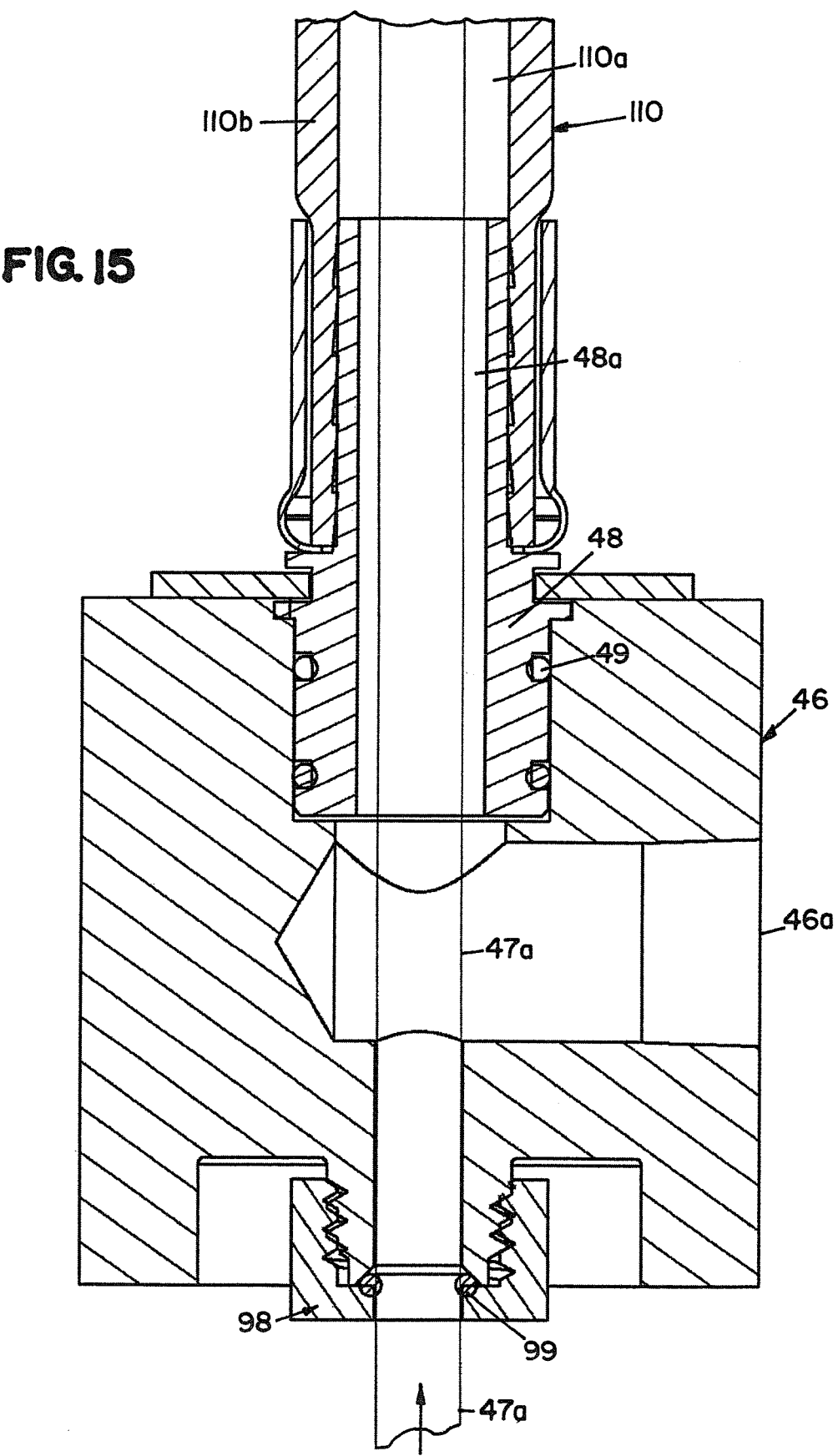
FIG. 15 is a cross-sectional view of the foam block shown in FIG. 3.
Figure 16:
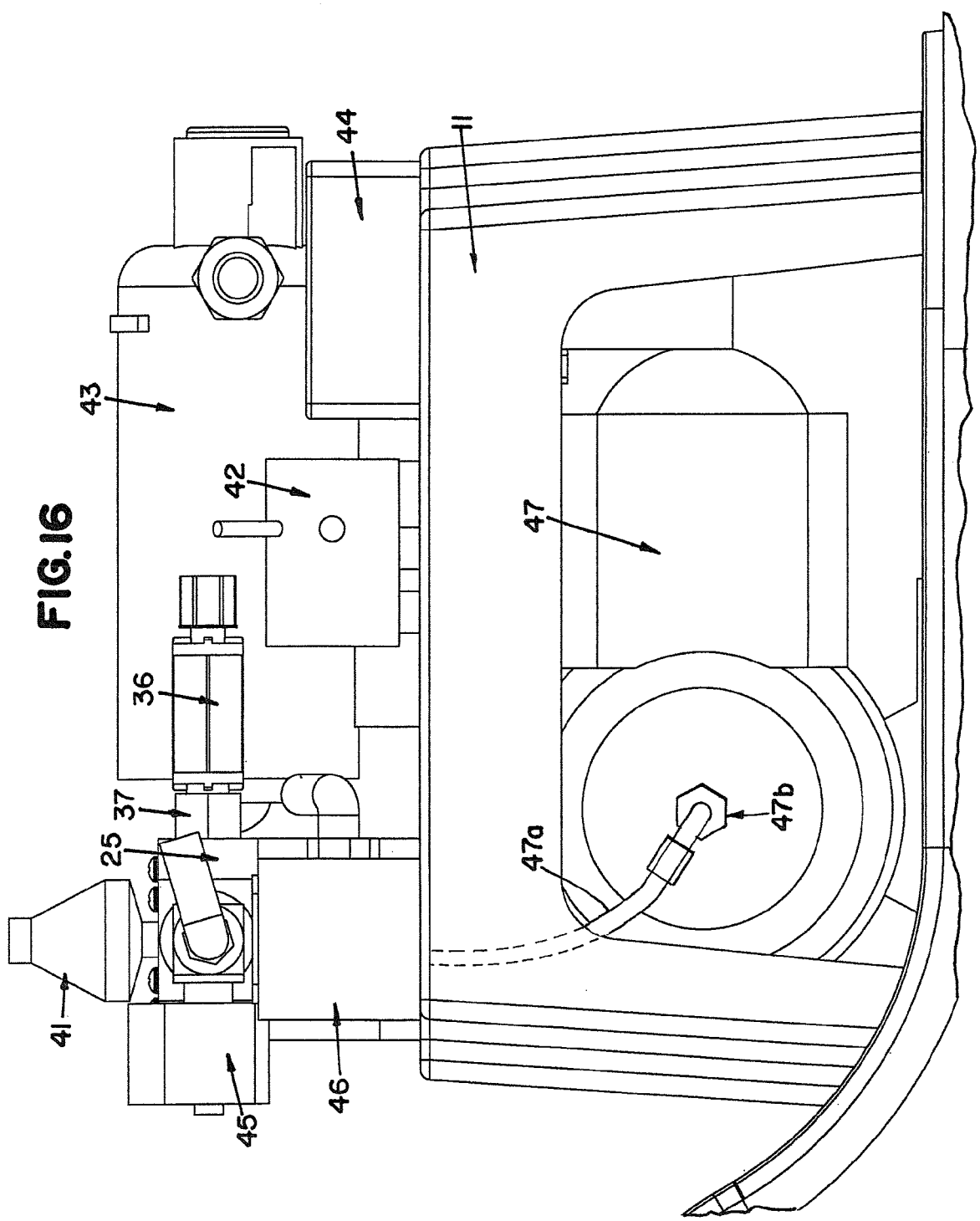
FIG. 16 is a component side view.

As the degreaser use solution exits the degreaser use solution outlet 31, the degreaser use solution travels through the water pump 43 and out the outlet 43b. The outlet 43b is then in fluid communication with the foam block 46. The block 46 is shown in FIG. 15. The function of the block 46 is to supply the first outlet hose 110 with both a degreaser use solution and compressed air. Compressed air is generated from the air compressor 47. An air line 47a is in fluid communication with the outlet of the air compressor 47 and is secured by means of an elbow 47b. The pressure that is generated by the air compressor is 130 psi or less and preferably 100 psi or less. This lower pressure provides for added safety for the operator. The line 47a enters the block 46 through a nut 98 that is secured to the block 46 and it utilizes and O-ring 99 that is positioned around the air line 47a. The air line 47a at that point is continuous and extends through the block 46 and through the bore 110a of the hose 110. The block 46 has an opening 46a through which a conduit 88 is inserted and secured with a nut 89 and appropriate seals. The conduit 88 is connected at the other end to the outlet 43b of the water pump 43. The water then enters the opening 43a and goes up through fitment 48 that is sealed with O-ring 49 to the block 46. The water will proceed around the outside of the line 47 still within the bore 48a of the fitment 48. The water then continues out of the fitment 48 into the hose 110 and travels between the outer wall 110b and the line 47a toward the foam gun 140.

Figure 14:
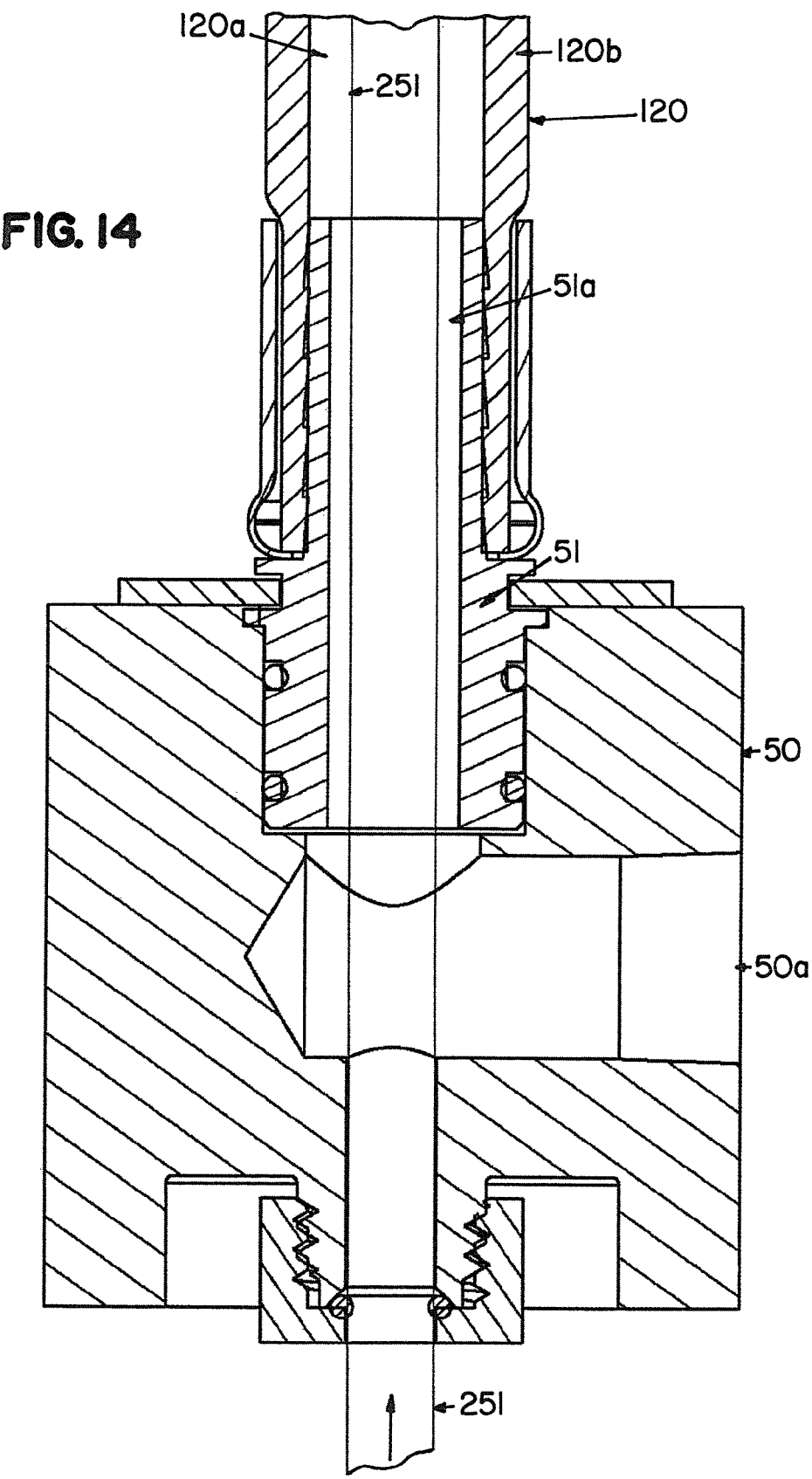
FIG. 14 is a cross-sectional view of the sanitizer block shown in FIG. 3.

A sanitizer block 50 is shown in FIG. 14 and is similar to the foam block 46. It is understood that the sizes and connections may vary, depending upon the specific design utilized. However, the function of the sanitizer block 50 is somewhat similar to that of the foam block 46. The sanitizer block 50 provides for a mechanism to provide both water and the sanitizer concentrate to the second outlet hose 120. The sanitizer block 50 has an opening 50*a* that is in fluid communication with the water outlet 30. A suitable conduit (not shown) places the outlet 30 in fluid communication with the opening 50*a* in a manner similar to the conduit 88 and nut 89 is utilized for the foam block 46. The liquid sanitizer concentrate moves from the sanitizer reservoir 250 through the conduit 251. The conduit 251 enters the bottom of the sanitizer block, as shown in FIG. 14 and extends up through the sanitizer block 50 through the second outlet hose 120. The water will enter the opening 50*a* and go up through the bore 51*a* of fitment 51 on the outside of the conduit 251. The water will then go into the outlet hose 120 and will be between the outer wall 120*b* and the conduit 251. The conduit 251 is in the bore 120*a* of the second outlet hose 120. The first outlet hose 110 and second outlet hose 120 are considered a hose assembly and are a hose-in-hose assembly. By such a construction, the two liquids or a liquid and compressed air are able to travel in one assembly, thereby making the handling of the hoses easier. There are only two hoses to handle, as opposed to four. Another construction would be to have the hoses separate, but secured to each other, such that the cross-section of the assembly would appear as a FIG. 8, with appropriate changes for connections to the blocks 46 and 50 and the foam gun 140 and the sanitizer gun 160. However, it is preferable to have a hose and hose construction as this reduces the overall volume in the hoses 110 and 120. This provides for a reduced volume of the hose 110 and 120, thereby allowing for improved hose management as well as increasing the amount of hose that may be stored on the racks 23, 24.

Figure 5:
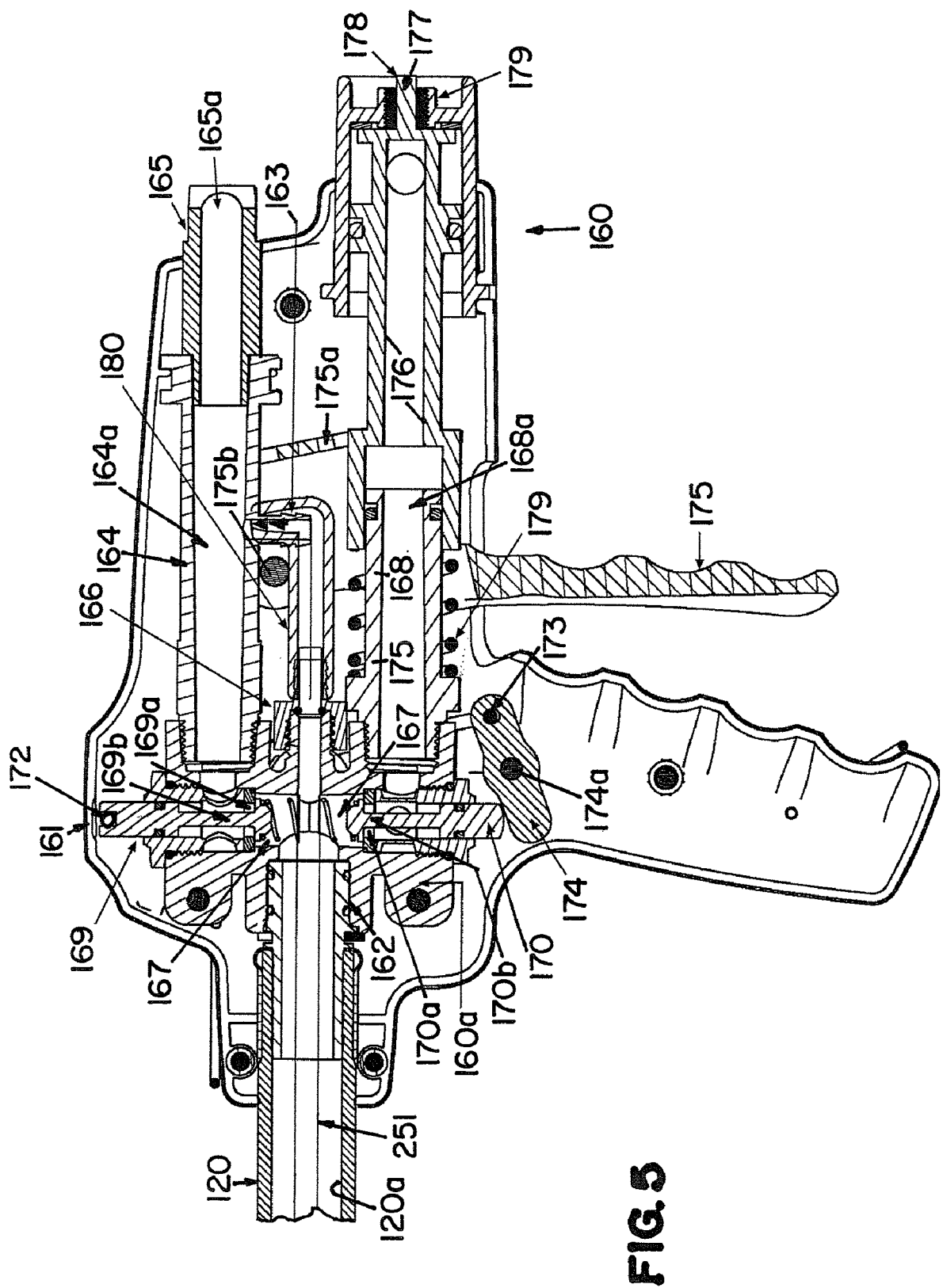
FIG. 5 is a cross-sectional view of a sanitizer gun for use with the mobile foam producing unit shown in FIG. 1.
Figure 6:
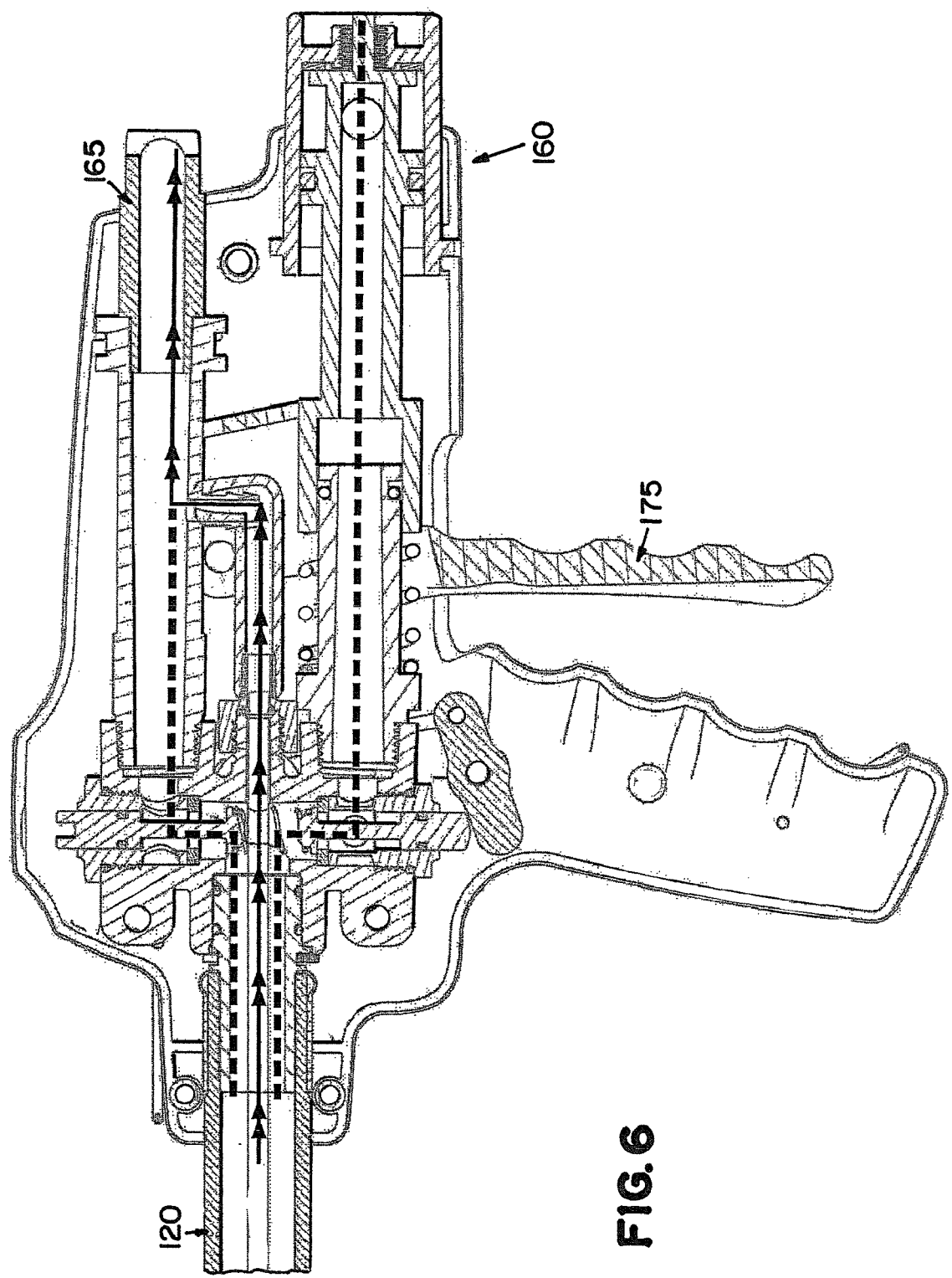
FIG. 6 is a cross-sectional view, similar to FIG. 5, showing a flow diagram thereof.
Figure 26:
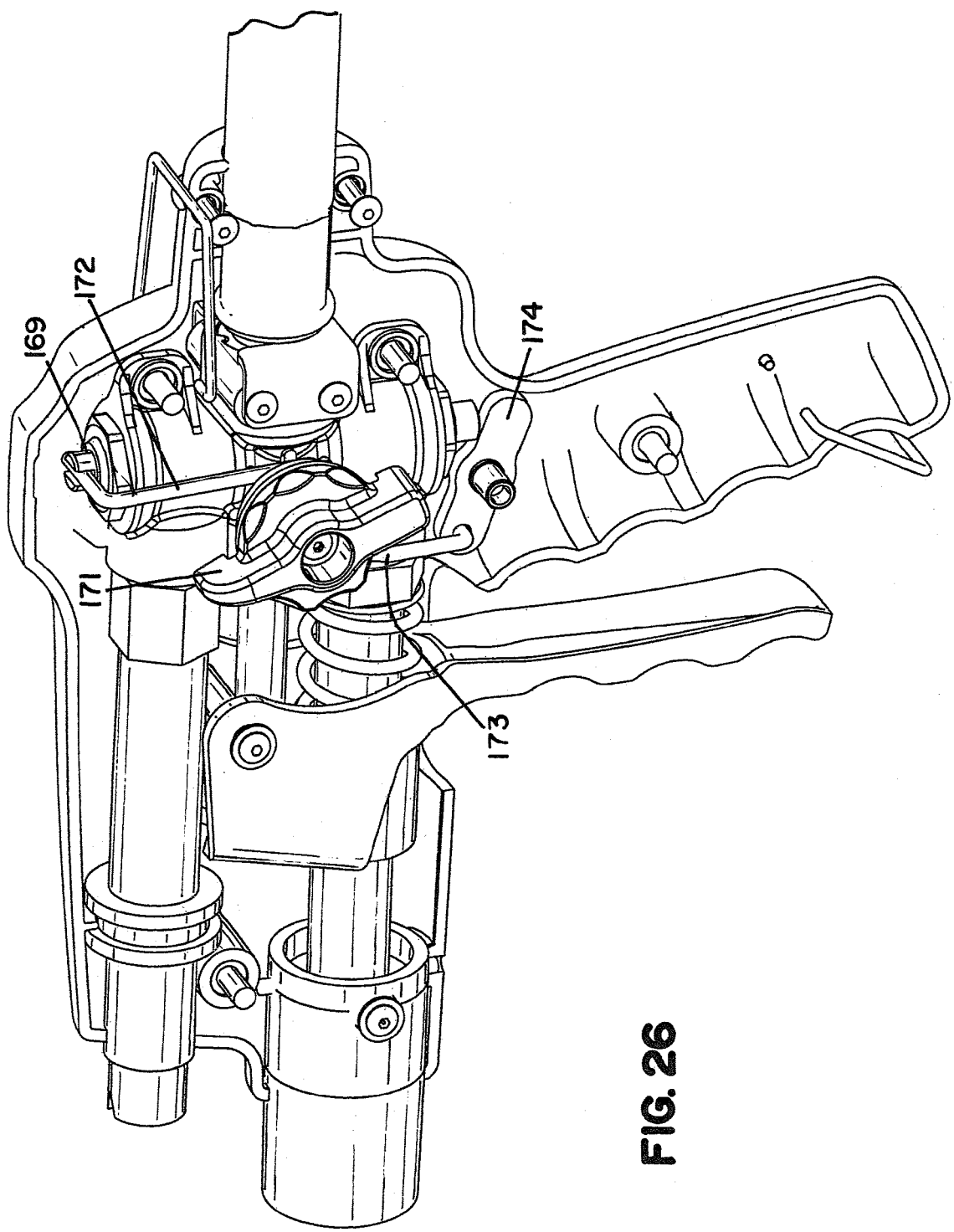
FIG. 26 is a perspective view of the sanitizer gun shown in FIG. 5, with portions of the outer housing broken away.

The sanitizer gun 160 is shown in more detail in FIGS. 5 and 6. The sanitizer gun 160 provides for the dispensing of the liquid sanitizer along with water in one mode of operation and just water in a second mode of operation. The gun 160 includes a housing 161. The second outlet hose 120 is secured in an opening in a manifold 160*a* in the housing 161 and sealed with O-rings 162. The sanitizer line 251 extends through the housing 151 to a metering tip 163. The metering tip 163 is positioned in a rubber elbow 180. The metering tip has an opening and extends into the sanitizer outlet bore 164*a* formed in the sanitizer dispensing tube 164. As will be described more fully hereinafter, movement of the water through the bore 164*a* will, by venturi effect, dispense the sanitizer through the metering tip 163 and into the bore 164*a* it will combine with the water and a sanitizer solution will exit the outlet 165*a* of the sanitizer spray fan 165. A brass standoff 166 is utilized to hold the sanitizer line 251 and the metering tip 163 in position. The water will enter the housing 161 into a chamber 167. The water is then directed either to the sanitizer dispenser tube 164 or the rinse dispenser tube 168 by operation of a first valve 169 and a second valve 170. The valve 169 has an opening 169*a* and flow from the chamber 167 through the opening 169*a* is controlled by valve stem 169*b*. FIG. 5 shows the valve stem 169*b* in an open position. Water is then able to flow around the valve stem 169*b* and into the bore 164*a*. The second valve 170 has an opening 170*a* that is sealed or opened by valve stem 170*b*. As shown in FIG. 5, the valve stem 170*b* is down and will close flow from the chamber 167 to the bore 168*a* of the rinse dispensing tube 168. A selector switch 171 controls the movement of the first valve 169 and second valve 170. As can be seen at FIG. 26, a first rod 172 is connected between the valve 169 and the selector switch 171 and a second rod 173 is connected between the selector switch 171 and a lever 174. Rotation of the selector switch 171 will result in the first valve 169 moving up and down by movement of the first rod 172 and will also result in the second rod 173 causing movement of the lever 174 about its pivot point 174*a*. This in turn will cause the second valve 170 to move up and down, as shown in FIG. 5. The selector switch 171 therefore opens one valve while closing the other valve. If, as shown in FIG. 5, the valves are in the positions shown, the water will move through the chamber 167 and out the bore 164*a* picking up liquid sanitizer as it exits. If the selector switch 171 is moved in the other direction, the valve stem 169*b* will close flow through the bore 164*a* and will allow flow from the chamber 167 to the bore 168*a*. However, water will not be able to exit the bore 168*a* unless the rinse trigger 175 is moved to the left, as shown in FIG. 5. The rinse dispenser tube 168 includes a first part 175 and a second part 176, that is slidable over the first part 175. A portion of the trigger 175*a* is operatively connected to the second part 176. Therefore, as a trigger 175 pivots about its pivot point 175*b*, the second part 176 is moved to the left, thereby moving the tip 177 away from the rinse outlet 178. This then will allow flow of the water from the bore 168*a* through the rinse outlet 178. A trigger spring 179 is provided to provide a biasing force on the second part 176 into the closed position. A brass hose sprayer tip 179 may be utilized to provide better control of the water exiting the rinse outlet 178.

FIG. 6 shows the flow of the sanitizer through the sanitizer gun 160. The line with a double arrow is the path traveled by the sanitizer concentrate and the dashed lines show the two alternative paths for the water. Strain relief 384 may be positioned on top of the housing 14, to reduce strain on the hoses 110, 120.

Figure 7:
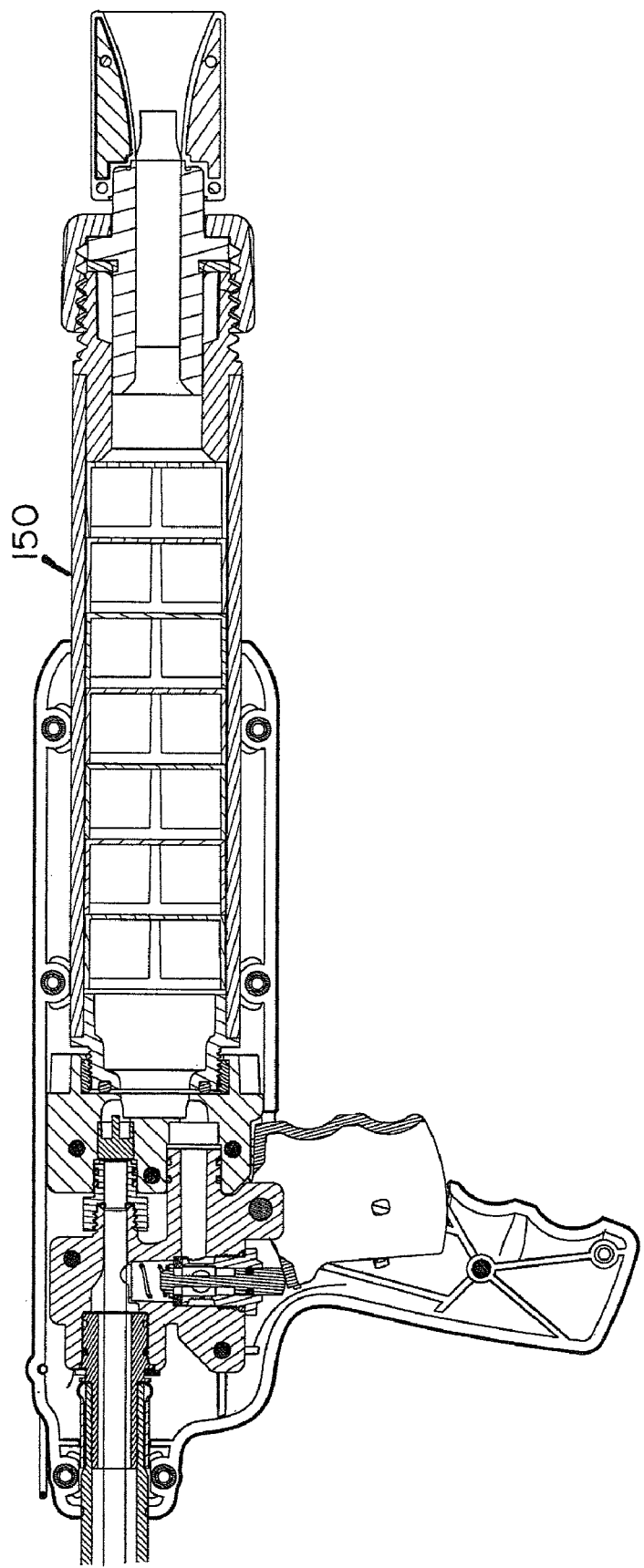
FIG. 7 is a cross-sectional view of a foam gun, for use with the mobile foam producing unit shown in FIG. 1.
Figure 27:
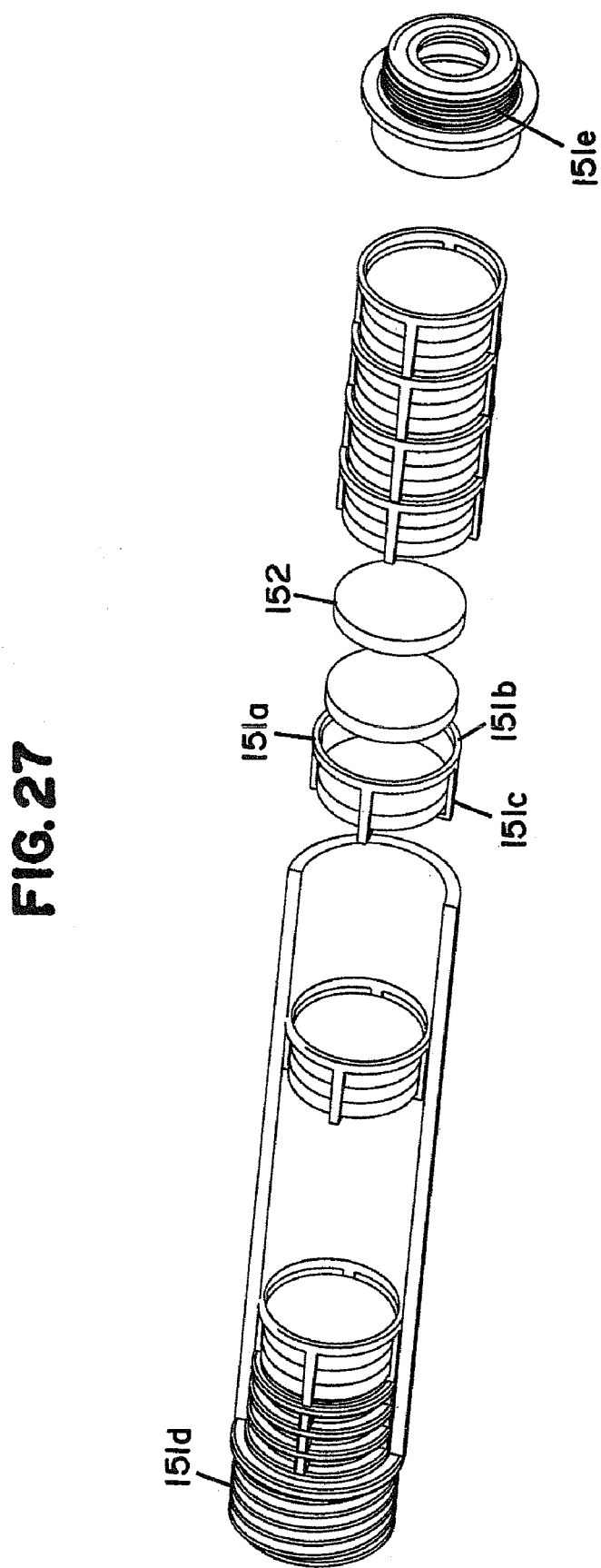
FIG. 27 is an exploded perspective of the media and media case shown in FIG. 7.

Referring now to FIGS. 7 and 8, there is shown in more detail the foam gun 140. The foam gun 140 includes a housing 141. A manifold 142 is positioned in the housing 141. The first outlet hose 110 is in fluid communication with the manifold 142 and is sealed by seals 143. The air line 47*a* extends through the manifold and is in fluid communication with an air check valve 144. The manifold 143 has a chamber 142*a* into which the degreaser use solution inside of the bore 110*a* empties. Flow out of the chamber 142*a* into bore 145 is controlled by valve assembly 146. The valve assembly 146 is shown in the closed position in FIG. 7. The valve stem 146*a* closes the opening 146*b* when in this position. Pulling back of the trigger 148 will cause rotation about its pivot point 140*a* and will move the valve assembly 146 upward. This will unseat the valve stem 146*a* from the opening 146*b* and allow degreaser use solution to flow into the bore 145. A plastic member 149 is positioned inside of the housing 141 and has a chamber 149*a* into which both of the compressed air, through air line 47*a* enters from the top and the degreaser use solution enters from the bottom from bore 145. The compressed air turns 90 degrees and impinges upon the degreaser use solution inside of the chamber 149*a* and the degreaser use solution and compressed air then travels through a foam cartridge 150. The foam cartridge 150 provides for the production of a quality foam as the compressed air and degreaser use solution travels through the foam cartridge 150. The foam cartridge 150 includes a media cage 150*a* that forms multiple circular compartments 151 *a*. Inside of the compartments 151 a are placed media disks 152. The compartments prevent the compression of the media disks 152 so as the media disks 152 maintain the desired density for producing foam. An exploded perspective of the media disks 152 and multiple circular compartments 151*a* is shown in FIG. 27. The media disks 152 are represented as a circular disk. It is understood that the general shape of the media disks 152 are circular. However, the media disks 152 are composed of a synthetic, non-woven material containing many interstitial spaces. Each individual disk 152 is a circular column with an approximate diameter of 4.454 cm and an approximate height of 0.76 cm. Each disk 152 weighs approximately 0.84 gm yielding a bulk density of 0.21 gm per cubic cm.

The media cage 150a includes seven multiple circular compartments 151a. Each of the compartments 151a hold three individual media disks 152 for a total of 21 media disks 152 per media cage 150a. The individual circular compartments 151a prevent the media disks 152 from becoming overly compressed by the flow of pressure of the foam solution, which would decrease the number of interstitial spaces, reducing turbulence which in turn would negatively impact the quality and stability of the foam produced. The circular compartments 151a form a basket. There is a top ring 151b with four supports 151c that extend underneath and are operatively connected together to form a basket in which the bottom of the three media disks 152 rests. To the left, in FIG. 27 is a threaded surface 151d that is threaded into the manifold. To the right is a threaded surface on 151e that is utilized to spray nozzle 153. The foam is then generated and exits the gun 140 through the fan spray nozzle 153. The foam is generated right at the point of use, the fan spray nozzle 153. This allows for a higher quality foam.

FIG. 8 shows the flow path of the water in a line with close dashes and the air with a line with longer dashes. Then, the mixing of the air and degreaser use solution in the foam cartridge 150 is shown by the crossing of the lines.

The foam produced by the mobile foam producing unit 10 has a high quality. There are two tests that are used to quantify the quality of foam. One is a blender/foam density/stability stance lubricity test. Such a test is discussed in the October 24 issue of *Cosmetics and Toiletries* magazine, Vol. 119, No. 10, p. 32-35. This test was modified slightly as it was not necessary to use a blender since the mobile foam producing unit 10 produces its own foam. In addition, instead of measuring between 80-40 ml, the test was measured between the two points 100 ml to 80 ml. The test that was conducted is as follows:

The foam is poured into a 100-ml graduated cylinder to overflowing. A rubber stopper is gently dropped into the foam. This stopper has been shaved so that it is slightly smaller in diameter than the inside of the graduated cylinder. The time for the rubber stopper to pass between two points (100-ml-80-ml) is measured. A longer time indicates denser and more stable foam. The rate at which the stopper falls is dependent on the upward pressure. This upward pressure is inversely proportional to the size of the bubbles. Thus, more dense foam will cause the rubber stopper to fall more slowly.

Most current foam products have a time of between 10 and 15 seconds using the above-noted test. The present invention consistently provides a high quality foam having a time of 25 seconds or greater. Further, the unit 10 produces a high quality foam having a time of 50 seconds or greater.

Another test is a drainage stability test. The drainage stability test is as follows:
1. Fill a 1000-ml graduated cylinder with foam.
2. Quickly remove excess foam from top using a flat stainless steel panel and start timer.
3. After 2 minutes, record liquid level (ml).
4. Continue taking liquid level readings every 2 minutes until:
   a. Foam has dissipated
   b. Ten readings (20 minutes)
   c. If the foam has not dissipated after 20 minutes, record at 20 minute intervals until dissipated
5. Measure the volume of the liquid after the foam is dissipated.

To Calculate the Volume of the Foam

1. Tare the empty, dry 1000-ml graduated cylinder.
2. Fill with water and record the weight.
3. Use the density of the water at room temperature to calculate the volume.
   The Unit Foam Ratio is:

$$\sigma = V_i \text{ foam}$$

$V_i$ foam = Initial volume of foam $V_i$ liquid $V_i$ liquid = Final volume of liquid 4. Plot the natural log of the measurements of the volume of the liquid versus time to find the relative foam stability constant.

The foam made in accordance with the present invention has a ratio of 6.0 and above and is typically 6.7. The typical prior art foam that is utilized has an average of between 4.8 to 5.4 for a ratio under the drainage stability test.

Figure 18:
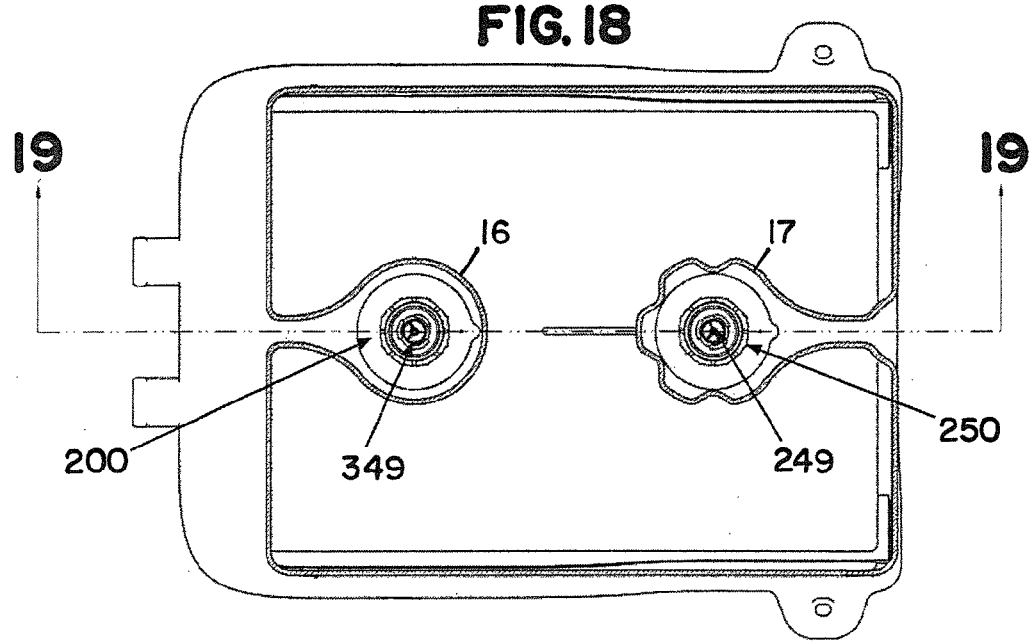
FIG. 18 is a cross-sectional view taken generally along the lines 18-18 in FIG. 2.
Figure 19:
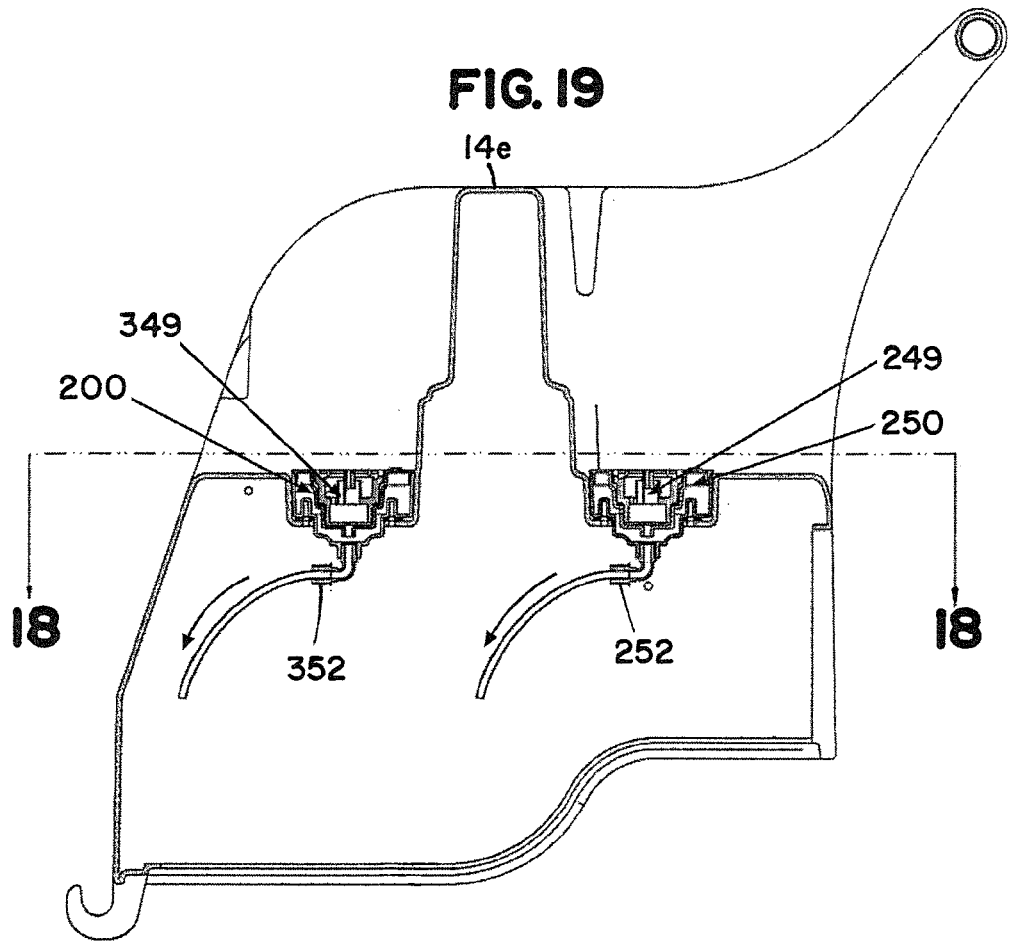
FIG. 19 is a cross-sectional view taken generally along the lines 19-19 in FIG. 18.
Figure 20:
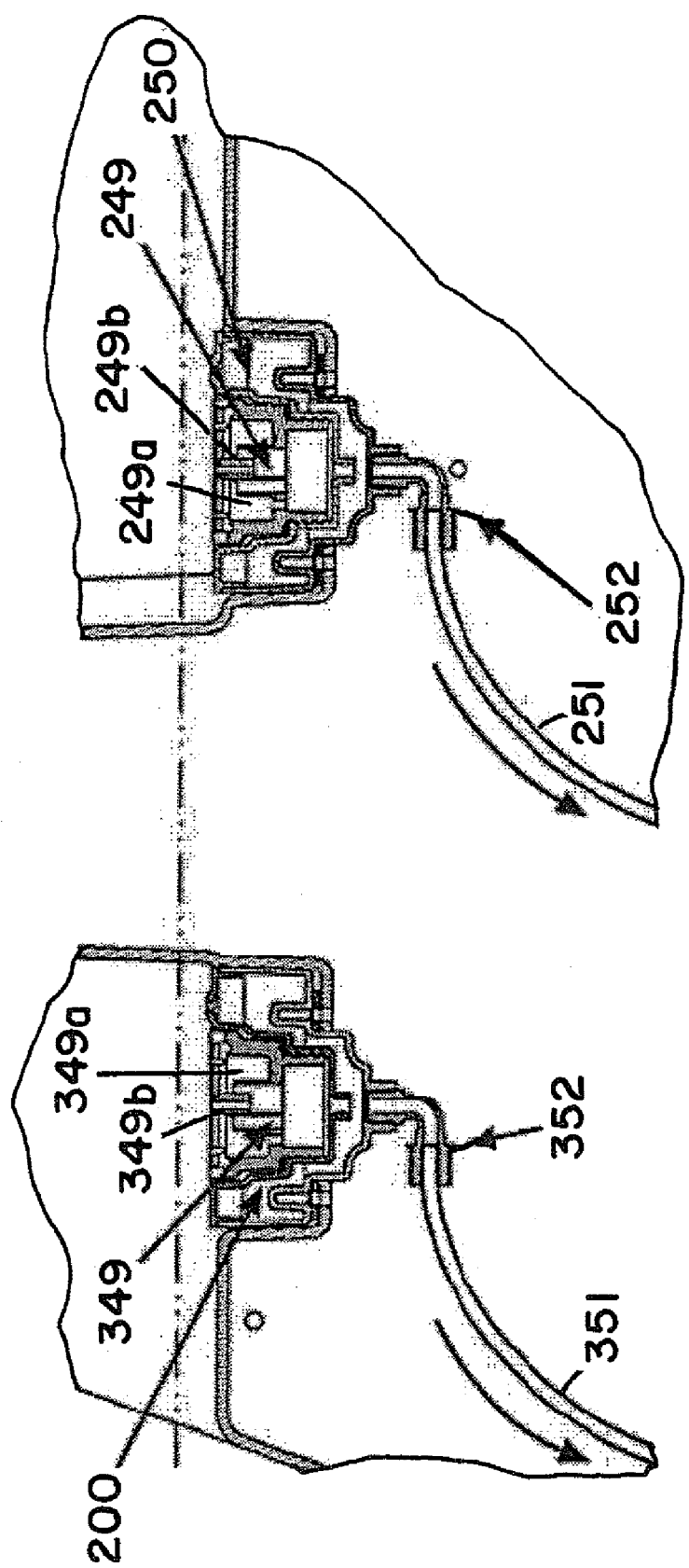
FIG. 20 is an enlarged view of a portion of FIG. 19.
Figure 21:
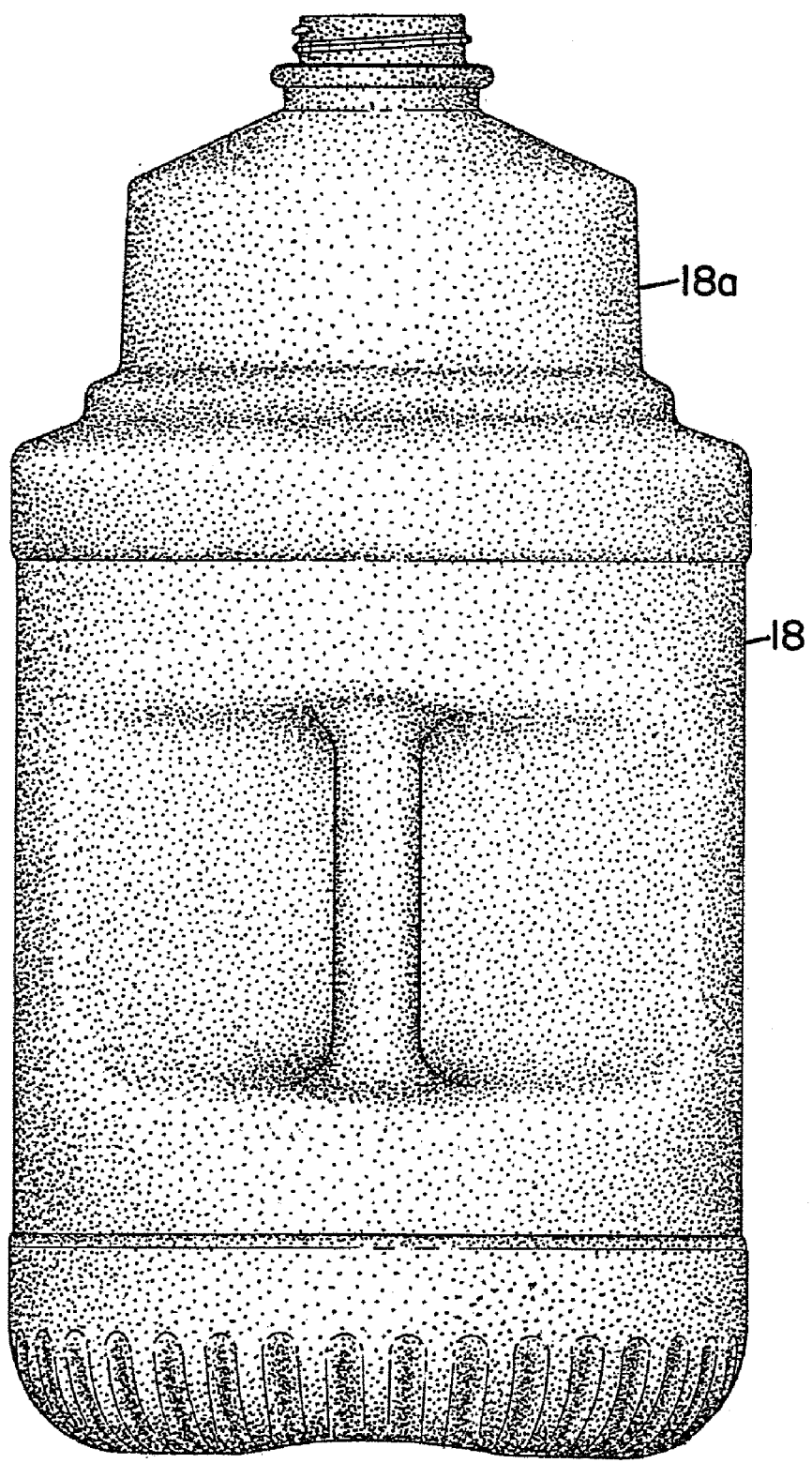
FIG. 21 is a side elevational view of a container for degreaser concentrate.
Figure 22:
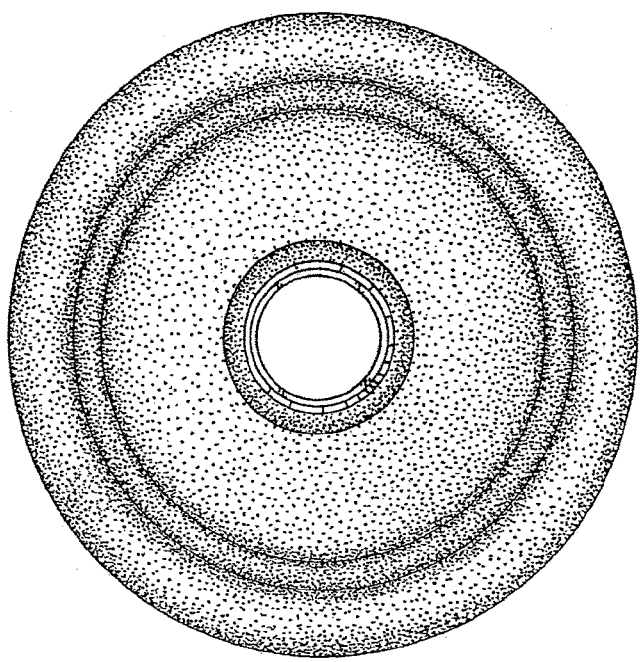
FIG. 22 is a top plan view of the container shown in FIG. 21.
Figure 24:
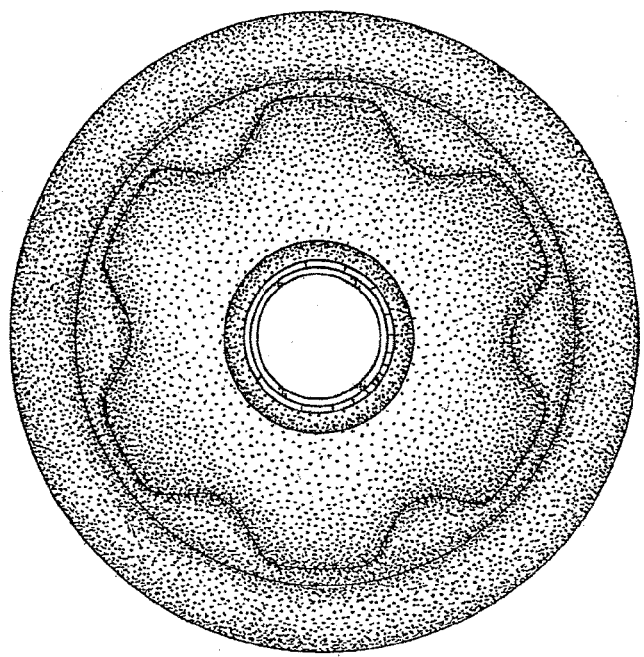
FIG. 24 is a top plan view of the container shown in FIG. 23.
Figure 23:
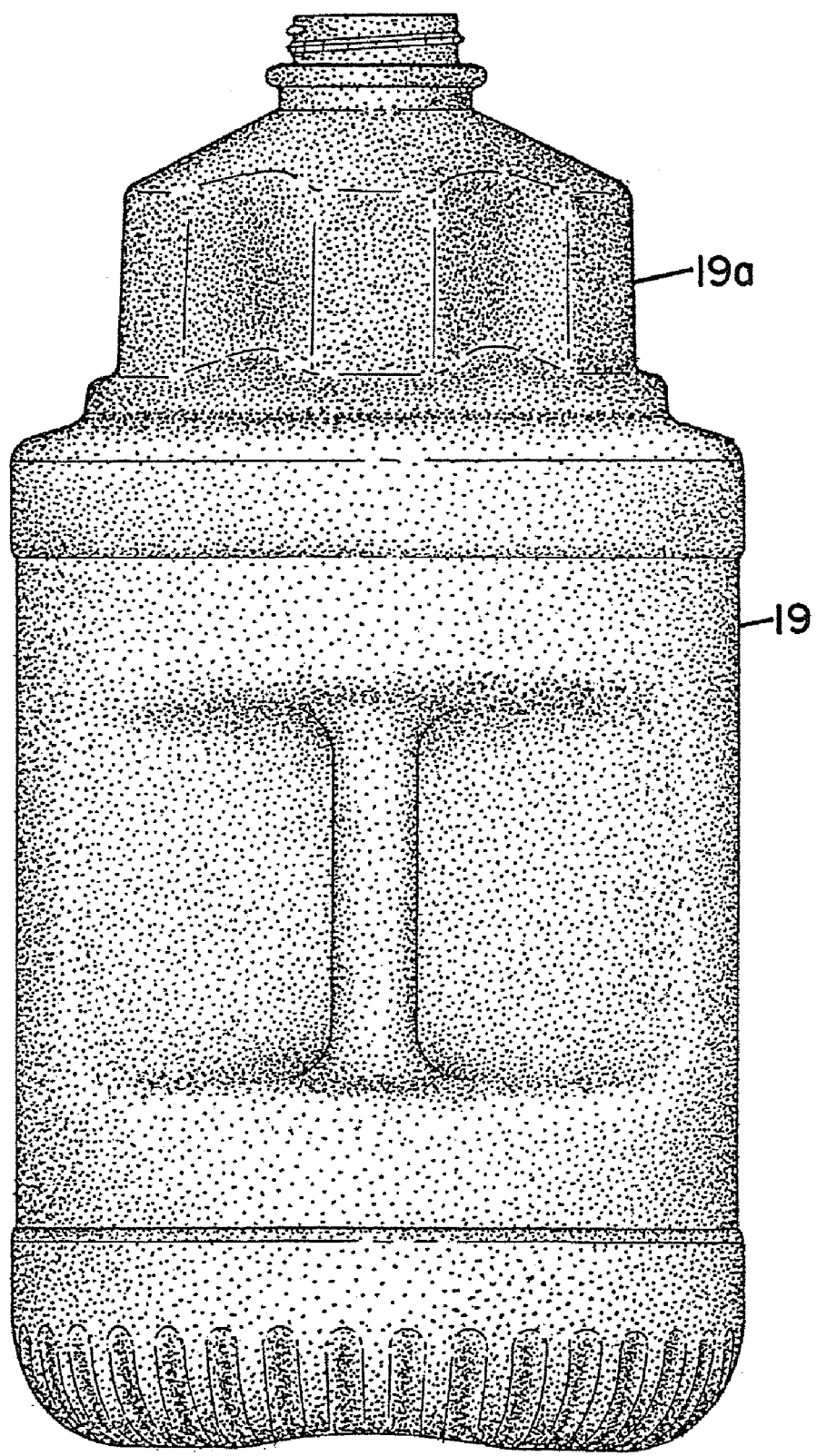
FIG. 23 is a side elevational view of a sanitizer container.

Referring now to FIGS. 18-20, it can be seen that the shape of the sanitizer compartment 17 formed by the housing 14 as well as the shape of the degreaser compartment 16 formed by the housing 14. The degreaser compartment 16 is generally circular and the sanitizer compartment 17 is hexagonal shaped. These shapes are designed to form a lockout with the degreaser container 18 and the sanitizer container 19. The container 18 has a circular top section 18a that is adapted and configured to fit within the degreaser compartment 16. Similarly, the container 19 has a hexagonal shaped top portion 19a that is designed and configured to fit into the comparably shaped sanitizer compartment 17. The shapes are designed so as to not be interchangeable. That is, the sanitizer container 19 will not fit within the degreaser compartment 16 and the degreaser container 18 will not fit within the sanitizer compartment 17. This prevents the accidental mix-up by an operator. A sanitizer docking cup 249 is positioned inside of the sanitizer reservoir 250. The sanitizer docking cup includes a chamber 249a for receiving the neck of the container 19. The neck of the container 19 includes a fitment that will cooperate with the docking member 249b that will allow liquid to drain from the container 19 through the member 249b into the reservoir 250. The liquid inside the container 19 will accumulate in the reservoir 250 and will exit the reservoir via the conduit 251. An elbow fitting 252 is utilized to connect the conduit 251 to the docking cup 249.

A degreaser docking cup 349 is positioned inside of the degreaser reservoir 200. The degreaser docking cup includes a chamber 349a for receiving the neck of the container 18. The neck of the container 18 includes a fitment that will cooperate with the docking member 349b that will allow liquid to drain from the container 18 through the member 349b into the reservoir 200. The liquid inside the container 18 will accumulate in the reservoir 200 and will exit the reservoir via the conduit 351 to the inlet of the peristaltic pump 44. An elbow fitting 352 is utilized to connect the conduit 351 to the docking cup 349.

Both of the bottles 18 and 19 are not vented. The water only goes through the fitment (not shown) in the neck of the containers. The vacuum created prevents the dispensing of the entire contents of the container 18 and 19 as long as there is fluid in the reservoirs 250 and 200. More specifically, the plunger insert in the bottle and the docking cups work together with pressure equilibriums. When the bottle is first docked on the docking cup, the plunger insert depresses and allows product to flow into the reservoir. Air bubbles enter the bottle through the liquid and allow the pressure to stabilize at equilibrium. The liquid column is held in the bottle by the vacuum created by the air head space. As the liquid column level decreases, less vacuum is needed to hold the liquid column in the bottle. Atmospheric air enters the bottle to place the system in equilibrium. The bottle thickness determines if the bottle will collapse. If the bottle has a hole in it, the vacuum is depleted and not enough to hold the liquid column. The product would then drain trying to establish an equilibrium. Such a system is known in the art and has been used by Ecolab Inc., St. Paul, Minn., in their AeroLite™ dispenser.

Figure 2:
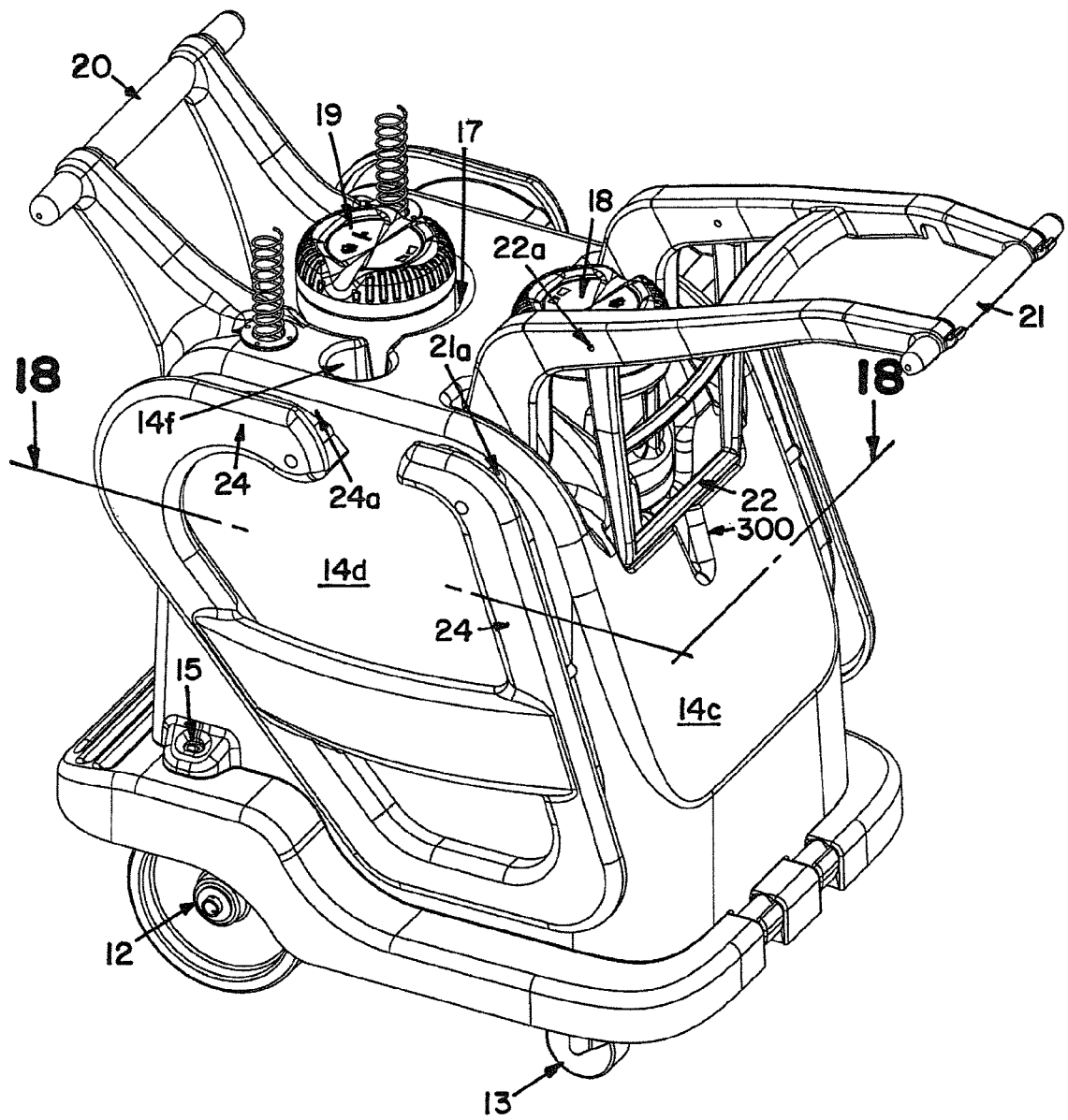
FIG. 2 is a perspective view of the mobile foam producing unit shown in FIG. 1 viewed generally from above and having been rotated 180 degrees from FIG. 1.

As seen in FIG. 2, a product overflow 300 is formed in the housing in the unlikely event that there is an excess of liquid in the reservoirs 200 and 250. As seen in FIG. 1, there is a charge adaptor port 301 that is operatively connected to a battery. The battery 500 is shown in FIG. 28, it being understood that suitable electrical connections are made from the battery 500 to power the unit 10.

Also, a battery LED indicator 302 is provided to show the status of the battery.

Referring now to FIG. 5, there is shown the mobile foam producing unit 10 in use with a wall mounted self-retractable reel 400. The self-retractable reel 400 is mounted to a wall 500 by a suitable means, such as bolts (not shown) through brackets 401. Preferably, the self-retractable reel is mounted 5-6 feet off of the floor. This gives more area to properly manage the hose 100. Still further, it is preferable that the self-retracting hose reel 400 be able to swivel 180 degrees on the brackets 401. The brackets 401 are attached to the retractable reel 400. The supply hose 100 is contained in the reel 400. Such a construction is well known. The hose 100 may be pulled out to have additional length. Then, when it is desired to retract, the hose 100 is simply pulled sharply forward and then it retracts to take up any slack. The municipal water supply is connected to the end of the hose in the reel 400. Typically a short section of hose, 4-6 feet, is used to connect the water faucet to the inlet of the hose 100. The other end of the hose 100 is in fluid communication with the water inlet 26 on the mobile foam producing unit 10. Preferably, a quick disconnect is operatively connected to the distal end. The quick disconnect then is designed to be connected to the water inlet 26. The mobile foam producing unit 10, in FIG. 25, shows the foam gun 140 ready to be used. That is, the hose 110 has been removed from the hose wrap 24. The sanitizer gun 160 is not being utilized so the second outlet hose 120 is wrapped around the first hose wrap 23 and is out of the way as the unit 10 may be maneuvered by either pushing or pulling on the handles 20 or 21. While it is shown that the hose 100 is a retractable hose in the retractable reel 400, it is also appreciated that other connections to a water supply may be utilized. For instance, utilizing appropriate connections, well known in the art, the hose 100 could be connected to a water outlet using a quick disconnect, as disclosed in U.S. application Ser. No. 10/074,594 entitled "Method and Apparatus for Cleaning a Surface" filed Feb. 12, 2002. However, it is recognized hose management would not be as effective with such a connection.

In use, the water supply from the spigot or faucet that receives water from the municipal water supply is turned on. This provides water to the supply hose 100. Then, a sufficient length of hose 100 is taken out of the self-retractable reel 400 and, using a quick disconnect coupling, the end of the hose 100 is connected to the water inlet 26. A suitable on/off valve (not shown) is also utilized to turn on the water and further control the municipal water supply. With these two valves turned on, water is then supplied through the hose 100 to the manifold 26. Once there is above approximately 7-8 psi of pressure in the water in the manifold 25, the water pressure sensor 41 is activated and this actuates the relay which in turn powers a starter solenoid valve. This in turn provides power to the water pump, air compressor and peristaltic pump. Typically, the operator will utilize the foam gun 140 first and will unwrap the hose 110. By depressing the trigger, a pressure sensor on the water pump is activated at the water pump 43 and provides water at a desired pressure. As previously described, this will generate a foam that is sprayed on the surfaces to be cleaned. Because of the high quality of foam, the foam will stay on the equipment being cleaned longer, and thereby provide a better cleaning of the work surface.

Next, the operator can wrap up the hose 110 on the hose wrap 24 and uncoil the hose 120 and utilize the sanitizer gun 160. As previously described, the selector switch 171 is turned to allow only the dispensing of water and the work surface is rinsed down. Then, the selector switch is rotated, as previously described, to allow the dispensing of the combination sanitizer and water. The hose 120 can then be wrapped back on the hose wrap 23, the two water valves turned off and the hose 100 disconnected from the mobile foam producing unit 10.

While the present invention has been described with respect to a degreaser (that foams) and a sanitizer, it is understood other cleaning concentrates may also be dispensed. Further, more than two could also be utilized, if the present invention is appropriately modified.

The above specification, examples and data provide a complete description of the manufacture and use of the composition of the invention. Since many embodiments of the invention can be made without departing from the spirit and scope of the invention, the invention resides in the claims hereinafter appended.

We claim:

1. A mobile foam producing unit for dispensing a first liquid and a second liquid using a municipal water supply providing water at a pressure of less than 100 psi, comprising:
(a) a base having a plurality of wheels;
(b) a housing operatively connected to the base, the housing having first, second, third and fourth sides, the housing having a first docking area for receiving a first liquid and a second docking area for receiving a second liquid;
(c) an air compressor for supplying compressed air operatively connected to the base;
(d) a water pump, having a water pump inlet and a water pump outlet, operatively connected to the base;
(e) a first hose assembly having a first outer hose and a first inner hose;
(f) a second hose assembly having a second outer hose and a second inner hose;
(g) a water inlet, the water inlet having a first opening adapted and configured to be connected to a municipal water supply and a second opening in fluid communication with the water pump inlet;
(h) a rechargeable battery operatively connected to the base, the rechargeable battery being used to power the air compressor and the water pump;
(i) the water inlet, through the water pump, in fluid communication with the first outer hose and the water inlet in fluid communication with the second outer hose;
(j) the first liquid in fluid communication with the first outer hose, wherein a use solution is made;

(k) the air compressor in fluid communication with the first inner hose;
(l) the second liquid in fluid communication with the second inner hose;
(m) a first spray gun operatively connected to a discharge end of the first hose assembly, whereby foam is dispensed by combining the use solution in the first outer hose and the compressed air in the first inner hose;
(n) a second spray gun operatively connected to a discharge end of the second hose assembly, the second spray gun having a selector valve for allowing separate dispensing of the water in the second outer hose and the second liquid in the second inner hose;
(o) a first hose rack operatively connected to a first side of the housing, wherein the first hose assembly is storable on the first hose rack; and
(p) a second hose rack operatively connected to a second side of the housing, wherein the second hose assembly is storable on the second hose rack.

2. The mobile foam producing unit of claim 1, further comprising:
(a) a first handle operatively connected to the unit proximate the third side of the housing; and
(b) a second handle operatively connected to the unit proximate the fourth side of the housing, the third side opposite the fourth side, wherein the unit is capable of being separately pushed and pulled from both the third and fourth sides.

3. The mobile foam producing unit of claim 1, further comprising the air compressor providing compressed air at less than 130 psi.

4. The mobile foam producing unit of claim 3, wherein the compressed air is less than 100 psi.

5. The mobile foam producing unit of claim 1, further comprising the water pump providing water at a pressure of less than 100 psi.

6. The mobile foam producing unit of claim 1, further comprising a flow control device in fluid communication with the first spray gun, the flow control device limiting flow from 1 to 2 gallons per minute.

7. The mobile foam producing unit of claim 1, further comprising:
(a) the first liquid provided in a first bottle having a first outer configuration;
(b) the first docking area having a first cross-sectional area matched to receive the first bottle outer configuration;
(c) the second liquid provided in a second bottle having a second outer configuration;
(d) the second docking area having a second cross-sectional area matched to receive the second bottle outer configuration;
(e) wherein a product lockout is created to prevent mixing of the liquids and the docking areas.

8. The mobile foam producing unit of claim 1, further comprising:
(a) a self-retracting hose reel operatively connected to a support surface; and
(b) a supply hose carried by the self-retracting hose reel, the supply hose having a first end adapted and configured to be connected to the municipal water supply and a second end in fluid communication with the water inlet, wherein the mobile foam producing unit has improved hose management of the first hose assembly, second hose assembly and the supply hose.

9. A mobile foam producing unit for dispensing a first liquid and a second liquid using a municipal water supply providing water at a pressure of less than 100 psi, comprising:
(a) a base having a plurality of wheels;
(b) a housing operatively connected to the base, the housing having first, second, third and fourth sides, the housing having a first docking area for receiving a first liquid and a second docking area for receiving a second liquid;
(c) an air compressor for supplying compressed air operatively connected to the base;
(d) a water pump, having a water pump inlet and a water pump outlet, operatively connected to the base;
(e) a first hose assembly having a first outer hose and a first inner hose;
(f) a second hose assembly having a second outer hose and a second inner hose;
(g) a water inlet, the water inlet having a first opening adapted and configured to be connected to a municipal water supply and a second opening in fluid communication with the water pump inlet;
(h) a rechargeable battery operatively connected to the base, the rechargeable battery being used to power the air compressor and the water pump;
(i) the water inlet, through the water pump, in fluid communication with the first outer hose and the water inlet in fluid communication with the second outer hose;
(j) the first liquid in fluid communication with the first outer hose, wherein a use solution is made;
(k) the air compressor in fluid communication with the first inner hose;
(l) the second liquid in fluid communication with the second inner hose;
(m) a first spray gun operatively connected to a discharge end of the first hose assembly, whereby foam is dispensed by combining the use solution in the first outer hose and the compressed air in the first inner hose;
(n) a second spray gun operatively connected to a discharge end of the second hose assembly, the second spray gun having a selector valve for allowing separate dispensing of the water in the second outer hose and the second liquid in the second inner hose;
(o) a first hose rack operatively connected to a first side of the housing, wherein the first hose assembly is storable on the first hose rack;
(p) a second hose rack operatively connected to a second side of the housing, wherein the second hose assembly is storable on the second hose rack;
(q) a first handle operatively connected to the unit proximate the third side of the housing;
(r) a second handle operatively connected to the unit proximate the fourth side of the housing, the third side opposite the fourth side, wherein the unit is capable of being separately pushed and pulled from both the third and fourth sides;
(s) the air compressor providing compressed air at less than 130 psi;
(t) the water pump providing water at a pressure of less than 100 psi;
(u) the first liquid provided in a first bottle having a first outer configuration;
(v) the first docking area having a first cross-sectional area matched to receive the first bottle outer configuration;
(w) the second liquid provided in a second bottle having a second outer configuration;
(x) the second docking area having a second cross-sectional area matched to receive the second bottle outer configuration, wherein a product lockout is created to prevent mixing of the liquids and the docking areas;
(y) a self-retracting hose reel operatively connected to a support surface; and (z) a supply hose carried by the self-retracting hose reel, the supply hose having a first end adapted and configured to be connected to the municipal water supply and a second end in fluid communication with the water inlet, wherein the mobile foam producing unit has improved hose management of the first hose assembly, second hose assembly and the supply hose.

10. A portable system to clean and disinfect a work area using a municipal water supply providing water at a pressure of less than 100 psi, using a cleaning concentrate and a liquid sanitizer, the system comprising:
    (a) a base having a plurality of wheels;
    (b) a housing operatively connected to the base, the housing having a first docking area for receiving a cleaning concentrate and a second docking area for receiving a liquid sanitizer;
    (c) an air compressor for supplying compressed air operatively connected to the base, the air compressor providing compressed air at less than 130 psi;
    (d) a first hose assembly having a first conduit and a second conduit, the second conduit carried by the first conduit;
    (e) a second hose assembly having a third conduit and a fourth conduit, the fourth conduit carried by the third conduit;
    (f) a water pump, having a water pump inlet and a water pump outlet, operatively connected to the base;
    (g) a water inlet, the water inlet having a first opening adapted and configured to be connected to receive water from a municipal water supply and a second opening in fluid communication with the water pump inlet;
    (h) the water from the water pump outlet is at a pressure less than 100 psi;
    (i) a foam spray gun in fluid communication with the water pump outlet and the cleaning concentrate, wherein a quality foam is produced; and
    (j) a sanitizer gun in fluid communication with the water inlet and the liquid sanitizer, the sanitizer gun having a selector valve for allowing the dispensing of both the water from the third conduit and the dispensing of a combination water from the third conduit and liquid sanitizer from the fourth conduit.

11. The portable system of claim 10, wherein the compressed air is less than 100 psi.

12. The portable cleaning system of claim 10, further comprising:
    (a) the second conduit of the first hose assembly is inside of the first conduit; and
    (b) the fourth conduit of the second hose assembly is inside of the third conduit.

13. The portable cleaning system of claim 12, further comprising the foam having a rating on a modification of foam quality test of 25 seconds or more.

14. The portable cleaning system of claim 13, wherein the foam has rating on a modification of foam quality test of 40 seconds or more.

15. The portable cleaning system of claim 12, further comprising the foam having unit foam ratio of 6.0 or greater.

16. The portable cleaning system of claim 15, wherein the unit foam ratio is 6.5 or greater.

17. The portable cleaning system of claim 10, the foam spray gun further comprising:
    (a) a foam cartridge having an inlet to receive the water and the cleaning concentrate and an outlet for dispensing foam created; and
    (b) a plurality of media disks positioned in the foam cartridge, through which the water and cleaning concentrate flow, the media disks comprising a synthetic, nonwoven material containing many interstitial spaces.

18. The portable cleaning system of claim 17, the foam cartridge further comprising a media case having a plurality of spaced dividers, wherein compression of the media disks is controlled, the disks having a density of 0.21 g/cm$^3$.

19. A portable system to clean and disinfect a work area using a municipal water supply providing water at a pressure of less than 100 psi, using a cleaning concentrate and a liquid sanitizer, the system comprising:
    (a) a base having a plurality of wheels;
    (b) a housing operatively connected to the base, the housing having a first docking area for receiving a cleaning concentrate and a second docking area for receiving a liquid sanitizer;
    (c) an air compressor for supplying compressed air operatively connected to the base, the air compressor providing compressed air at less than 130 psi;
    (d) a first hose assembly having a first conduit and a second conduit, the second conduit carried by the first conduit;
    (e) a second hose assembly having a third conduit and a fourth conduit, the fourth conduit carried by the third conduit;
    (f) a water pump, having a water pump inlet and a water pump outlet, operatively connected to the base;
    (g) a water inlet, the water inlet having a first opening adapted and configured to be connected to receive water from a municipal water supply and a second opening in fluid communication with the water pump inlet;
    (h) the water from the water pump outlet is at a pressure less than 100 psi;
    (i) a foam spray gun in fluid communication with the water pump outlet and the cleaning concentrate, wherein a quality foam is produced;
    (j) a flow control device in fluid communication with the spray gun, the flow control device limiting flow from 1 to 2 gallons per minute;
    (k) a sanitizer gun in fluid communication with the water inlet and the liquid sanitizer, the sanitizer gun having a selector valve for allowing the dispensing of both the water from the third conduit and the dispensing of a combination water from the third conduit and liquid sanitizer from the fourth conduit;
    (l) the foam having a rating on a modification of foam quality test of 25 seconds or more; and
    (m) the foam having unit foam ratio of 6.0 or greater.

* * * * *